(12) United States Patent
Wichelecki

(10) Patent No.: US 11,034,988 B2
(45) Date of Patent: *Jun. 15, 2021

(54) ENZYMATIC PRODUCTION OF D-TAGATOSE

(71) Applicant: BONUMOSE, INC., Charlottesville, VA (US)

(72) Inventor: Daniel Joseph Wichelecki, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,961

(22) Filed: Jan. 7, 2020

(65) Prior Publication Data
US 2020/0199637 A1   Jun. 25, 2020

Related U.S. Application Data

(63) Continuation of application No. 16/145,887, filed on Sep. 28, 2018, now Pat. No. 10,533,202, which is a continuation of application No. 15/743,481, filed as application No. PCT/US2016/054838 on Sep. 30, 2016, now Pat. No. 10,138,506.

(60) Provisional application No. 62/236,226, filed on Oct. 2, 2015.

(51) Int. Cl.
*C12P 19/02* (2006.01)
*C12N 9/90* (2006.01)

(52) U.S. Cl.
CPC ............... *C12P 19/02* (2013.01); *C12N 9/90* (2013.01); *C12Y 207/01144* (2013.01)

(58) Field of Classification Search
None
See application file for complete search history.

(56) References Cited

U.S. PATENT DOCUMENTS

| | | | |
|---|---|---|---|
| 5,002,612 A | 3/1991 | Beadle et al. | |
| 6,057,135 A | 5/2000 | Ibrahim et al. | |
| 8,211,681 B2 | 7/2012 | Zhang et al. | |
| 8,802,843 B2 | 8/2014 | Oroskar et al. | |
| 9,914,919 B2 | 3/2018 | Oh et al. | |
| 10,138,506 B2 * | 11/2018 | Wichelecki | C12P 19/02 |
| 10,533,202 B2 * | 1/2020 | Wichelecki | C12N 9/90 |
| 2008/0299622 A1 | 12/2008 | Paulson et al. | |
| 2016/0028101 A1 | 1/2016 | Zhang et al. | |
| 2016/0138053 A1 | 5/2016 | Yang et al. | |
| 2016/0186162 A1 | 6/2016 | Oh et al. | |
| 2017/0306370 A1 | 10/2017 | Kim et al. | |
| 2018/0023073 A1 | 1/2018 | Oh | |
| 2018/0057844 A1 | 3/2018 | Zhang et al. | |

FOREIGN PATENT DOCUMENTS

| | | |
|---|---|---|
| CA | 2912540 A1 | 12/2014 |
| CN | 102373230 A | 3/2012 |
| CN | 102827855 A | 12/2012 |
| CN | 103025894 A | 4/2013 |
| CN | 103131721 A | 6/2013 |
| CN | 104471771 A | 3/2015 |
| CN | 104988166 A | 10/2015 |
| CN | 106148425 A | 11/2016 |
| CN | 106399427 A | 2/2017 |
| CN | 106811493 A | 6/2017 |
| CN | 107208084 A | 9/2017 |
| JP | 2013143962 A | 7/2013 |
| JP | 2013535962 A | 9/2013 |
| JP | 2014239651 A | 12/2014 |
| KR | 1020060059622 A | 6/2006 |
| KR | 1020140133680 A | 11/2014 |
| KR | 101480422 B1 | 1/2015 |
| KR | 101620904 B1 | 5/2016 |
| KR | 101636058 B1 | 6/2016 |
| KR | 101765684 B1 | 8/2017 |
| KR | 20170116978 A | 10/2017 |
| KR | 20170116979 A | 10/2017 |
| KR | 20170117860 A | 10/2017 |
| KR | 20180008256 A | 1/2018 |
| KR | 20180013815 A | 2/2018 |
| WO | 2005/084411 A2 | 9/2005 |
| WO | 2011/150556 A1 | 12/2011 |
| WO | 2013/150069 A1 | 10/2013 |
| WO | 2015/016544 A1 | 2/2015 |
| WO | 2017/059278 A1 | 4/2017 |
| WO | 2018/004310 A1 | 1/2018 |

OTHER PUBLICATIONS

Chica et al. Curr Opin Biotechnol. Aug. 2005;16(4):378-84. (Year: 2006).*
Singh et al. Curr Protein Pept Sci. 2017, 18, 1-11 (Year: 2017).*
GenBank Accession AP012029.1, dated Jan. 25, 2011.
Pakula et al., "Genetic Analysis of Protein Stability and Function", Annu. Rev. Genet, 1989, 23:289-310.
Van Der Maarel and Leemhuis "Starch modification with microbial alpha-glucanotransferase enzymes", Carbohydrate Polymers 93, 2013, 116-121.
Bosshart et al., "Directed Divergent Evolution of a Thermostable D-Tagatose Epimerase towards Improved Activity for Two Hexose Substrates", ChemBioChem, 2015, 16, pp. 592-601.
Details:DSM-25992, Culture Detailed Price Information for Clostridium thermocellum, https://www.dsmz.de/catalogues/details/culture/DSM-25992, accessed Jun. 4, 2019.

(Continued)

*Primary Examiner* — Christian L Fronda
(74) *Attorney, Agent, or Firm* — J.A. Lindeman & Co., PLLC

(57) ABSTRACT

The current disclosure provides a process for enzymatically converting a saccharide into tagatose. The invention also relates to a process for preparing tagatose where the process involves converting fructose 6-phosphate (F6P) to tagatose 6-phosphate (T6P), catalyzed by an epimerase, and converting the T6P to tagatose, catalyzed by a phosphatase.

9 Claims, 9 Drawing Sheets
Specification includes a Sequence Listing.

(56) References Cited

OTHER PUBLICATIONS

Enzyme: 2.4.1.1; https://www.kegg.jp/dbget-bin/www.bget?ec:2.4.1.1; accessed Jun. 4, 2019.
Enzyme: 2.4.1.8; https://www.kegg.jp/dbget-bin/www.bget?ec:2.4.1.8; accessed Jun. 4, 2019.
Enzyme: 5.4.2.6; https://www.kegg.jp/dbget-bin/www.bget?ec:5.4.2.6; accessed Jun. 4, 2019.
Gao et al., "Production of rare sugars from common sugars in subcritical aqueous ethanol", Food Chemistry, 2015, 175; pp. 465-470.
Gaspar et al., "From physiology to systems metabolic engineering for the production of biochemicals by lactic acid bacteria ", Biotechnology Advances 31, 2013, pp. 764-788.
Glucose 1-Phosphate=Glucose 6-Phosphate, http://equilibrator.weizmann.ac.il/search?query=GLUCOSE+1-PHOSPHATE%3DGLUCOSE+6-PHOSPHATE&x=0&y=0; accessed Jun. 4, 2019.
Glucose 6-Phosphate=Fructose- 6-Phosphate, http://equilibrator.weizmann.ac.il/search?query=GLUCOSE+6-PHOSPHATE%3DFructose-6-PHOSPHATE&x=7&y=13; accessed Jun. 4, 2019.
Jeon et al., Eur. J. Biochem., 248, (1997); pp. 171-178.
Liu et a., Process Biochemistry 51 (2016); pp. 1458-1463.
Shin et al., Journal of Industrial Microbiology & Biotechnology (2000), 24, pp. 89-93.
Xu et al., Biochemical Engineering Journal 109 (2016), pp. 28-34.
Zhou et al., J. Agric. Food Chem. 2016, 64, pp. 1777-1783.
English Translation of Jingyan Wang et al. "Biochemistry", Higher Education Press, third edition, Aug. 2002: relevant pp. 146/277-152/277.
Third Party Observation in International Application No. PCT/US2016/054838, filed Feb. 1, 2018.
Huang et al., "Panoramic view of a superfamily of phosphatases through substrate profiling", PNAS Apr. 21, 2015, Supporting Information, Download Dataset_S01; Excel file available at https://doi.org/10.1073/pnas.1423570112.
Huang et al., "Panoramic view of a superfamily of phosphatases through substrate profiling", PNAS Apr. 21, 2015, Supporting Information, Download Dataset_S02; Excel file available at https://doi.org/10.1073/pnas.1423570112.
Hansen et al., "Bifunctional Phosphoglucose/Phosphomannose Isomerases from the Archaea Aeropyrum permix and Thermoplasma acidophilum Constitute a Novel Enzyme Family within the Phosphoglucose Isomerase Supeifamily", J. Biological Chemistry, 2004, vol. 279, No. 3, pp. 2262-2272.
Opposition filed in CN Application No. 201610937656.5, dated Mar. 26, 2018.
First Office Action in CN Application No. 201610937656.5, dated Oct. 23, 2017.
Second Office Action in CN Application No. 201610937656.5, dated Feb. 9, 2018.
First Amended Complaint filed in The United District Court for the Western District of Virginia, Charlottesville Division, Civil Action No. 3:17-cv-00033, dated Aug. 15, 2017.
Defendant's Response to Dismiss Plaintiff's First Amended Complaint filed in The United District Court for the Western District of Virginia, Charlottesville Division, Civil Action No. 3:17-cv-00033, dated Sep. 11, 2017.
Rashid et al., "Among Multiple Phosphomannomutase Gene Orthologues, Only One Gene Encodes a Protein with Phosphoglucomutase and Phosphomannomutase Activities in Thermococcus kodakaraensis," Journal of Bacteriology, Sep. 2004, p. 6070-6076 vol. 186, No. 18.
Suwan Myung and Y-H Percival Zhang, "Ultra-stable phosphoglucose isomerase through immobilization of cellulose-binding module-tagged thermophilic enzyme on low-cost high-capacity cellulosic adsorbent," Biotechnology Progress, Jul. 2011;27(4):969-75.
Litigation document production Part 1 from Case No. 3:17-cv-00033, bates ranges CFB00000001-CFB00000022 and CFB00000976-CFB00001033 received Jun. 12, 2018.
Litigation document production Part 2 from Case No. 3:17-cv-00033, bates ranges CFB00001034-CFB00001123, received Jun. 12, 2018.
Litigation document production Part 3 from Case No. 3:17-cv-00033, bates ranges CFB00001125-CFB00001224, received Jun. 12, 2018.
Litigation document production Part 4 from Case No. 3:17-cv-00033, bates ranges CFB00001225-CFB00001323 and CFB00009190-CFB00009197.
Cheng et al., "Doubling Power Output of Starch Biobattery Treated by the Most Thermostable Isoamylase from an Archaeon Sulfolobus tokodaii", Scientific Reports, 2015, 5:13184, pp. 1-10.
Van Der Heiden et al., "A Pathway Closely Related to the D-Tagatose Pathway of Gram-Negative Enterobacteria Identified in the Gram-Positive Bacterium Bacillus licheniformis", Applied and Environmental Microbiology, 2013, vol. 79, No. 11, pp. 3511-3515.
Wen et al., "Facile Enzymatic Synthesis of Ketoses", Angew Chem. Int. Ed. Engl., 2015, 54(43): 12654-12658.
Zhang et al., "Enzymatic approaches to rare sugar production", Biotechnol. Adv., 2017, pp. 1-8.
Accession D2RHV2, dated Sep. 16, 2015.
Accession F2KMK2, dated Jun. 24, 2015.
Accession E8N0N6, dated Jul. 22, 2015.
Accession E4SEH3, dated Jul. 22, 2015.
Accession H1XRG1, dated Jul. 22, 2015.
Accession I0I507, dated Jul. 22, 2015.
Li et al. "Biosynthesis of rare hexoses using microorganisms and related enzymes", Beilstein J. Org. Chern. 2013. vol. 9, pp. 2434-2445.
Wichelecki et al., "ATP-binding Cassette (ABC) Transport System Solute-binding Protein-guided Identification of Novel D-Altritol and Galactitol Catabolic Pathways in Agrobacterium tumefaciens C58*s", The Journal of Biological Chemistry vol. 290, No. 48, pp. 28963-28976, Nov. 27, 2015.
Huang et al., "Panoramic view of a superfamily of phosphatases through substrate profiling", pp. E1974-E1983, PNAS, Published online Apr. 6, 2015.
Chan et al., "Structural Basis for Substrate Specificity in Phosphate Binding ($\beta/\alpha$)8-Barrels: D-Allulose 6-Phosphate 3-Epimerase from *Escherichia coli* K-12†", NIH Public Access, Biochemistry,Sep. 9, 2008; 47(36), pp. 9608-9617.
CJ Cheiljedang, "D. Physico-Chemcal properties of D-tagatose:", Tagatose GRAS notice Aug. 2, 2010, pp. 4-7.
Moradian et al., "A Biomimetic Biotechnological Process for Converting Starch to Fructose: Thermodynamic and Evolutionary Considerations in Applied Enzymology", J. Am. Chem. Soc. 1992, 114, pp. 6980-6987.
Wichelecki et al., "Supplementary Information", Discovery of Novel D-Altritol and Galactitol Catabolic Pathways, pp. 1-4.
Accession A3DBX9, Mar. 20, 2007.
Accession O29805, dated Jan. 1, 1998.
Accession B5YBD7, dated Nov. 25, 2008.
Accession Q68BJ6, dated Oct. 11, 2004.
Chica et al., Curr Opin Biotechnol. Aug. 2005: 16(4): 378-84.
Singh et al., Curr Protein Pept Sci. 2017, 18, 1-11.
Ohdan et al., J Biotechnol. Jan. 10, 2007: 127(3): 496-502.
Rathore et a., Crit Rev Biotechnol. 2009: 29(3): 214-24.

\* cited by examiner

SEQUENCE LISTING

```
<160> NUMBER OF SEQ ID NOS: 17

<210> SEQ ID NO 1
<211> LENGTH: 1287
<212> TYPE: DNA
<213> ORGANISM: Anaerolinea thermophila UNI-1

<400> SEQUENCE: 1
atgttcggct cgcctgctcc cctgctggat atggtcaccg cgcagaaaca gggcatggcg      60
cggggtatcc catccatttg ttcggcacat ccggtggtgc tgagtgccgc ctgccatctt     120
gcccgccgga gcggcgcgcc cctgctcatc gaaaccacct gcaatcaggt caaccaccaa     180
```

-continued

```
ggtgggtaca gcggcatgac ccccgccgat tttgtccgct ttctgcgcga aattctggaa    240
cgggaaggta ttccccccgca acaggtcatc ctgggcgggg atcacctggg tccttacccc    300
tggcggaaag agcctgccga aaccgccata gcacaagcgc tggaaatggt gcgggcatac    360
gtgcaggcag gctacaccaa aattcatctg gacgcttcca tgccctgcgc cgatgacgac    420
cccgagcgtc ccctgccgct ggagcgcata gcccgacggg cggcgcagtt gtgcgccgcc    480
gccgaagccg ccgcgggagc ggttcagccg gtgtacgtaa ttggcagtga ggtgcccccg    540
cccggcggcg cgcagggtca ggaggcaaga cttcacgtca ccactccgca ggaagcccaa    600
gccgcgctgg atgcctttcg ggaagccttt ctgcaggcag gcttgactcc cgtttgggag    660
cgggtcattg cgctggtagt ccagccgggg gtggagtttg gcgtggacag cattcacgcc    720
tatcagcgcg aagccgcccg cccgctgaag accttcatcg agggcgtgcc cggcatggtg    780
tatgaagccc actcgaccga ttaccagacc cgtgcctccc tgcgtgcgct ggtggaagac    840 cactttttcca ttctcaaggt tggtccggca ctaaccttttg cctaccgcga agccgtgttc    900
gccctggaac acatcgaacg ggaaatattg gcaggcagg atatgcctct ctcccgcctg    960
agtgaagtcc tcgacgaggt gatgctgaac gatccacgcc actggcaggg atactttgcc   1020
ggcgctcccg ccgaacaggc gctggcgcgc cgctacagtt tcagcgaccg cattcgctat   1080
tactggcacc atcccgccgc gcaggaagcc gtgcggagac tgctcgccaa cctgatcgaa   1140
accccgccgc cgctgagttt gctcagccag tacctgccgc gcgagtatga gatggtgcgc   1200 gcggggggaaa tctccagcca cccgcaggac ctgattcggg cacatatcca gcacacgctg   1260
gaagattacg ctgcggcgtg cgggtaa                                        1287
```

<210> SEQ ID NO 2
<211> LENGTH: 428
<212> TYPE: PRT
<213> ORGANISM: Anaerolinea thermophila UNI-1

<400> SEQUENCE: 2

```
Met Phe Gly Ser Pro Ala Pro Leu Leu Asp Met Val Thr Ala Gln Lys
1               5                   10                  15

Gln Gly Met Ala Arg Gly Ile Pro Ser Ile Cys Ser Ala His Pro Val
            20                  25                  30

Val Leu Ser Ala Ala Cys His Leu Ala Arg Arg Ser Gly Ala Pro Leu
        35                  40                  45

Leu Ile Glu Thr Thr Cys Asn Gln Val Asn His Gln Gly Gly Tyr Ser
    50                  55                  60

Gly Met Thr Pro Ala Asp Phe Val Arg Phe Leu Arg Glu Ile Leu Glu
65                  70                  75                  80

Arg Glu Gly Ile Pro Pro Gln Gln Val Ile Leu Gly Gly Asp His Leu
                85                  90                  95

Gly Pro Tyr Pro Trp Arg Lys Glu Pro Ala Glu Thr Ala Ile Ala Gln
            100                 105                 110

Ala Leu Glu Met Val Arg Ala Tyr Val Gln Ala Gly Tyr Thr Lys Ile
        115                 120                 125

His Leu Asp Ala Ser Met Pro Cys Ala Asp Asp Pro Glu Arg Pro
    130                 135                 140

Leu Pro Leu Glu Arg Ile Ala Arg Arg Ala Ala Gln Leu Cys Ala Ala
145                 150                 155                 160

Ala Glu Ala Ala Ala Gly Ala Val Gln Pro Val Tyr Val Ile Gly Ser
                165                 170                 175
```

| | | | | | | | | | | | |
|---|---|---|---|---|---|---|---|---|---|---|---|
|Glu|Val|Pro|Pro|Gly|Gly|Ala|Gln|Gly|Gln|Glu|Ala|Arg|Leu|His|
| | | |180| | | |185| | | |190| | | |

Val Thr Thr Pro Gln Glu Ala Gln Ala Ala Leu Asp Ala Phe Arg Glu
            195                 200                 205

Ala Phe Leu Gln Ala Gly Leu Thr Pro Val Trp Glu Arg Val Ile Ala
        210                 215                 220

Leu Val Val Gln Pro Gly Val Glu Phe Gly Val Asp Ser Ile His Ala
225                 230                 235                 240

Tyr Gln Arg Glu Ala Ala Arg Pro Leu Lys Thr Phe Ile Glu Gly Val
                245                 250                 255

Pro Gly Met Val Tyr Glu Ala His Ser Thr Asp Tyr Gln Thr Arg Ala
            260                 265                 270

Ser Leu Arg Ala Leu Val Glu Asp His Phe Ser Ile Leu Lys Val Gly
        275                 280                 285

Pro Ala Leu Thr Phe Ala Tyr Arg Glu Ala Val Phe Ala Leu Glu His
    290                 295                 300

Ile Glu Arg Glu Ile Leu Gly Arg Gln Asp Met Pro Leu Ser Arg Leu
305                 310                 315                 320

Ser Glu Val Leu Asp Glu Val Met Leu Asn Asp Pro Arg His Trp Gln
                325                 330                 335

Gly Tyr Phe Ala Gly Ala Pro Ala Glu Gln Ala Leu Ala Arg Arg Tyr
            340                 345                 350

Ser Phe Ser Asp Arg Ile Arg Tyr Tyr Trp His His Pro Ala Ala Gln
        355                 360                 365

Glu Ala Val Arg Arg Leu Leu Ala Asn Leu Ile Glu Thr Pro Pro Pro
    370                 375                 380

Leu Ser Leu Leu Ser Gln Tyr Leu Pro Arg Glu Tyr Glu Met Val Arg
385                 390                 395                 400

Ala Gly Glu Ile Ser Ser His Pro Gln Asp Leu Ile Arg Ala His Ile
                405                 410                 415

Gln His Thr Leu Glu Asp Tyr Ala Ala Ala Cys Gly
            420                 425

<210> SEQ ID NO 3
<211> LENGTH: 1290
<212> TYPE: DNA
<213> ORGANISM: Caldicellulosiruptor kronotskyensis

<400> SEQUENCE: 3

```
atgagtcctc aaaatccatt gattggttta tttaagaata gagaaaaaga gtttaagggt      60
attatttcag tttgttcttc aaatgaaata gtcttagaag cagttttaaa aagaatgaaa     120
gatacaaacc taccaattat tattgaagcc acagcgaacc aggtaaatca atttggcggg     180
tattctgggt tgacaccgtc tcagttcaaa gaacgagtta taaaaattgc tcaaaaagtt     240
gattttccac ttgagagaat aattcttggt ggggaccatc ttggaccatt tgtgtggcgt     300
gaccaggaac agaaattgc tatggagtat gctaagcaaa tgataaaaga atacataaaa      360
gcaggtttta ccaaaattca catcgacacg agtatgcctt aaaaggggga gacagcata      420
gatgatgaaa taattgctaa agaactgctg tgctctgca ggattgcgga ggagtgtttt      480
gagaagattt ctataaacaa tccctatatt acaaggccag tttatgtgat aggagctgat     540
gtgccacctc ccggcggaga gtcttctatt tgtcaaacaa ttactactaa agatgaatta     600
gaaagaagtt tagaatattt caagaagca tttaaaagg aaggaattga gcatgtattc       660
gattatgtag ttgctgttgt tgcaaatttt ggagttgaat ttgggagcga tgaaattgtt     720
```

```
gattttgata tggaaaaagt aaagccgcta aagaactttt tggcaaagta caatatagta    780
tttgaaggcc attctacaga ttatcaaaca aagaaaact taaaagaat ggtcgaatgt      840 ggtattgcaa ttttaaaggt tggtcctgct ctaacattta cattgcgcga agcgttagta   900
gcacttagtc atattgaaga agaaatttat agcaatgaaa aggagaaact gtcaagattt   960
agagaagttt tattgaatac tatgctaaca tgcaaagatc actggagtaa atattttgat  1020
gagaatgata agtaattaa gtcaaagctc ctatatagct atcttgacag atggagatac   1080
tattttgaaa acgagagtgt gaaaagtgct gtttattctc ttattggaaa tttagagaat  1140
gttaaaattc caccttggct tgtaagtcag tatttttcctt ctcagtacca aaagatgaga  1200
aaaaaagatt taaaaaacgg tgctgccgac ctaatattgg ataaaatagg ggaagtcatt  1260
gaccattatg tttatgcggt aaaagaataa                                    1290
```

<210> SEQ ID NO 4
<211> LENGTH: 429
<212> TYPE: PRT
<213> ORGANISM: Caldicellulosiruptor kronotskyensis

<400> SEQUENCE: 4

```
Met Ser Pro Gln Asn Pro Leu Ile Gly Leu Phe Lys Asn Arg Glu Lys
1               5                   10                  15

Glu Phe Lys Gly Ile Ile Ser Val Cys Ser Ser Asn Glu Ile Val Leu
            20                  25                  30

Glu Ala Val Leu Lys Arg Met Lys Asp Thr Asn Leu Pro Ile Ile Ile
        35                  40                  45

Glu Ala Thr Ala Asn Gln Val Asn Gln Phe Gly Gly Tyr Ser Gly Leu
    50                  55                  60

Thr Pro Ser Gln Phe Lys Glu Arg Val Ile Lys Ile Ala Gln Lys Val
65                  70                  75                  80

Asp Phe Pro Leu Glu Arg Ile Ile Leu Gly Gly Asp His Leu Gly Pro
                85                  90                  95

Phe Val Trp Arg Asp Gln Glu Pro Glu Ile Ala Met Glu Tyr Ala Lys
            100                 105                 110

Gln Met Ile Lys Glu Tyr Ile Lys Ala Gly Phe Thr Lys Ile His Ile
        115                 120                 125

Asp Thr Ser Met Pro Leu Lys Gly Glu Asn Ser Ile Asp Asp Glu Ile
    130                 135                 140

Ile Ala Lys Arg Thr Ala Val Leu Cys Arg Ile Ala Glu Glu Cys Phe
145                 150                 155                 160

Glu Lys Ile Ser Ile Asn Asn Pro Tyr Ile Thr Arg Pro Val Tyr Val
                165                 170                 175

Ile Gly Ala Asp Val Pro Pro Gly Gly Glu Ser Ser Ile Cys Gln
            180                 185                 190

Thr Ile Thr Thr Lys Asp Glu Leu Glu Arg Ser Leu Glu Tyr Phe Lys
        195                 200                 205

Glu Ala Phe Lys Lys Glu Gly Ile Glu His Val Phe Asp Tyr Val Val
    210                 215                 220

Ala Val Val Ala Asn Phe Gly Val Glu Phe Gly Ser Asp Glu Ile Val
225                 230                 235                 240

Asp Phe Asp Met Glu Lys Val Lys Pro Leu Lys Glu Leu Leu Ala Lys
                245                 250                 255

Tyr Asn Ile Val Phe Glu Gly His Ser Thr Asp Tyr Gln Thr Lys Glu
            260                 265                 270
```

```
        Asn Leu Lys Arg Met Val Glu Cys Gly Ile Ala Ile Leu Lys Val Gly
            275                 280                 285

Pro Ala Leu Thr Phe Thr Leu Arg Glu Ala Leu Val Ala Leu Ser His
            290                 295                 300

Ile Glu Glu Ile Tyr Ser Asn Glu Lys Lys Leu Ser Arg Phe
        305                 310                 315                 320

Arg Glu Val Leu Leu Asn Thr Met Leu Thr Cys Lys Asp His Trp Ser
                        325                 330                 335

Lys Tyr Phe Asp Glu Asn Asp Lys Leu Ile Lys Ser Lys Leu Leu Tyr
                            340                 345                 350

Ser Tyr Leu Asp Arg Trp Arg Tyr Tyr Phe Glu Asn Glu Ser Val Lys
                        355                 360                 365

Ser Ala Val Tyr Ser Leu Ile Gly Asn Leu Glu Asn Val Lys Ile Pro
            370                 375                 380

Pro Trp Leu Val Ser Gln Tyr Phe Pro Ser Gln Tyr Gln Lys Met Arg
        385                 390                 395                 400

Lys Lys Asp Leu Lys Asn Gly Ala Ala Asp Leu Ile Leu Asp Lys Ile
                            405                 410                 415

Gly Glu Val Ile Asp His Tyr Val Tyr Ala Val Lys Glu
                            420                 425

<210> SEQ ID NO 5
<211> LENGTH: 1227
<212> TYPE: DNA
<213> ORGANISM: Caldilinea aerophila

<400> SEQUENCE: 5
atgtcaacac ttcgccacat cattttgcga ctgatcgagc tgcgtgaacg agaacagatc    60
catctcacgc tgctggccgt ctgtcccaac tcggcggcgg tgctggaggc agcggtgaag   120
gtcgccgcgc gctgccacac gccgatgctc ttcgctgcca cgctcaatca gtcgatcgc    180 gacggcggct acaccggttg gacgcctgcg caattcgtcg ccgagatgcg tcgctatgcc   240
gtccgctatg gctgcaccac cccgctctat ccttgcctgg atcacggcgg gccgtggctc   300
aaagatcgcc atgcacagga aaagctaccg ctcgaccagg cgatgcatga ggtcaagctg   360
agcctcaccg cctgtctgga ggccggctac gcgctgctgc acatcgaccc cacggtcgat   420
cgcacgctcc cgcccggaga agcgccgctc gtgccgatcg tcgtcgagcg cacggtcgag   480
ctgatcgaac atgccgaaca ggagcgacag cggctgaacc tgccggcggt cgcctatgaa   540
gtcggcaccg aagaagtaca tggcgggctg gtgaatttcg acaattttgt cgccttcttg   600
gatttgctca aggcaaggct tgaacaacgt gccctgatgc acgcctggcc cgccttcgtg   660
gtggcgcagg tcggcactga cctgcataca acgtattttg accccagtgc ggcgcaacgg   720
ctgactgaga tcgtgcgccc taccggtgca ctgttgaagg ggcactacac cgactgggtc   780
gaaaatcccg ccgactatcc gagggtaggc atggaggcg ccaacgttgg tccagagttt   840
acggcggccg agttcgaggc gctggaagcg ctggaacggc gggaacaacg gctgtgcgcc   900
aaccggaaat tgcagcccgc ctgtttttg gctgcactgg aagaggcagt agtcgcttca   960
gatcgttggc ggaagtggct ccagcccgat gagatcggca gcccttttgc agaattaacg  1020
cccgcacgcc ggcgctggct cgtgcagacc ggggcacgct acgtctggac tgcgccgaaa  1080
gttatcgccg cacgcgaaca gctctatgcg cacctctccc ttgtgcaggc ggatccacat  1140
gcctacgtgg tagagtcagt cgcccggtca atcgagcgct atatcgatgc cttcaactta  1200
```
tacgacgccg ctacattgct tggatga                                      1227

<210> SEQ ID NO 6
<211> LENGTH: 408
<212> TYPE: PRT
<213> ORGANISM: Caldilinea aerophila

<400> SEQUENCE: 6

Met Ser Thr Leu Arg His Ile Ile Leu Arg Leu Ile Glu Leu Arg Glu
1               5                   10                  15

Arg Glu Gln Ile His Leu Thr Leu Leu Ala Val Cys Pro Asn Ser Ala
            20                  25                  30

Ala Val Leu Glu Ala Ala Val Lys Val Ala Ala Arg Cys His Thr Pro
        35                  40                  45

Met Leu Phe Ala Ala Thr Leu Asn Gln Val Asp Arg Asp Gly Gly Tyr
    50                  55                  60

Thr Gly Trp Thr Pro Ala Gln Phe Val Ala Glu Met Arg Arg Tyr Ala
65                  70                  75                  80

Val Arg Tyr Gly Cys Thr Thr Pro Leu Tyr Pro Cys Leu Asp His Gly
                85                  90                  95

Gly Pro Trp Leu Lys Asp Arg His Ala Gln Glu Lys Leu Pro Leu Asp
            100                 105                 110

Gln Ala Met His Glu Val Lys Leu Ser Leu Thr Ala Cys Leu Glu Ala
        115                 120                 125

Gly Tyr Ala Leu Leu His Ile Asp Pro Thr Val Asp Arg Thr Leu Pro
    130                 135                 140

Pro Gly Glu Ala Pro Leu Val Pro Ile Val Val Glu Arg Thr Val Glu
145                 150                 155                 160

Leu Ile Glu His Ala Glu Gln Glu Arg Gln Arg Leu Asn Leu Pro Ala
                165                 170                 175

Val Ala Tyr Glu Val Gly Thr Glu Glu Val His Gly Gly Leu Val Asn
            180                 185                 190

Phe Asp Asn Phe Val Ala Phe Leu Asp Leu Leu Lys Ala Arg Leu Glu
        195                 200                 205

Gln Arg Ala Leu Met His Ala Trp Pro Ala Phe Val Val Ala Gln Val
    210                 215                 220

Gly Thr Asp Leu His Thr Thr Tyr Phe Asp Pro Ser Ala Ala Gln Arg
225                 230                 235                 240

Leu Thr Glu Ile Val Arg Pro Thr Gly Ala Leu Leu Lys Gly His Tyr
                245                 250                 255

Thr Asp Trp Val Glu Asn Pro Ala Asp Tyr Pro Arg Val Gly Met Gly
            260                 265                 270

Gly Ala Asn Val Gly Pro Glu Phe Thr Ala Ala Glu Phe Glu Ala Leu
        275                 280                 285

Glu Ala Leu Glu Arg Arg Glu Gln Arg Leu Cys Ala Asn Arg Lys Leu
    290                 295                 300

Gln Pro Ala Cys Phe Leu Ala Ala Leu Glu Glu Ala Val Val Ala Ser
305                 310                 315                 320

Asp Arg Trp Arg Lys Trp Leu Gln Pro Asp Glu Ile Gly Lys Pro Phe
                325                 330                 335

Ala Glu Leu Thr Pro Ala Arg Arg Trp Leu Val Gln Thr Gly Ala
            340                 345                 350

Arg Tyr Val Trp Thr Ala Pro Lys Val Ile Ala Ala Arg Glu Gln Leu
        355                 360                 365

Tyr Ala His Leu Ser Leu Val Gln Ala Asp Pro His Ala Tyr Val Val
    370                 375                 380

Glu Ser Val Ala Arg Ser Ile Glu Arg Tyr Ile Asp Ala Phe Asn Leu
385                 390                 395                 400

Tyr Asp Ala Ala Thr Leu Leu Gly
                405

<210> SEQ ID NO 7
<211> LENGTH: 1362
<212> TYPE: DNA
<213> ORGANISM: Caldithrix abyssi

<400> SEQUENCE: 7

```
atgagtctgc atccttaaa taaattaatc gagcgacaca aaaaggaac gccggtcggt      60
atttattccg tctgttcggc caatccctt gttttgaaag cggccatgct acaggcgcaa    120
aaggatcagt ctttgctact tattgaggcc acttccaacc aggtagatca attcggcggt    180
tacaccggca tgcggcccga agattttaaa acaatgacgc ttgaactggc agccgaaaac    240
aattacgatc acagggatt aatcctgggc ggcgaccatc tggggcccaa ccgctggaca    300
aaactgagcg cctcccggc catggactac gccagagagc agattgccgc ttatgttaaa    360
gccggctttt ccaaaatcca cttagacgcc accatgccct gcaaaacga tgccacagat    420
tccgccggcc gccttccagt cgaaacaatc gctcaacgta ccgcagaatt atgcgccgtg    480
gccgaacaaa cttaccggca gagcgaccaa ctctttccgc cgcctgttta cattgtcggc    540
agcgacgtgc ccatcccggg cggcgcgcaa gaagcgctga ccagatcca tattacggag    600
gtaaaagagg ttcaacagac cattgatcac gtgcggcggg cctttgaaaa aaacggcctg    660
gaagcggctt acgaaagagt ttgcgccgtt gtcgtgcagc caggcgttga attcgccgat    720
caaatcgttt ttgaatacgc tcccgacaga gcggcggcct aaaagatttt tattgaaagc    780
cattcgcagc tggtttatga agcgcactct actgattacc agaccgcacc tcttttgcgc    840
cagatggtaa aagatcactt tgccatttta aaggtcgggc ctgcgctcac ctttgccctg    900
cgcgaagcca ttttgctct ggcctttatg gaaaaagagc ttttgccatt gcacagagcg    960
ctcaaacctt ctgccattct ggaaacgctg gaccaaacga tggacaaaaa ccctgcttac   1020
tggcaaaagc attacggcgg aacaaaggaa gaagtacgct ttgcgcagcg gtttagcctg   1080
agcgaccgca ttcgttacta ctggccgttt ccaaggttc aaaaggccct gcgccaattg   1140
ctaaaaaact tgcaacaaat ttccattcct ctaactttgg taagccagtt catgccagag   1200
gaataccaac gtattcgcca aggaacgtta accaacgatc cgcaggcgct gattttgaac   1260
aaaattcaaa gcgtattaaa gcaatacgcg gaggcgacgc aaattcaaaa ctctttgaca   1320
ttcacgcaaa atcaaaattc attagcaatg gagcgactat ga                     1362
```

<210> SEQ ID NO 8
<211> LENGTH: 453
<212> TYPE: PRT
<213> ORGANISM: Caldithrix abyssi

<400> SEQUENCE: 8

Met Ser Leu His Pro Leu Asn Lys Leu Ile Glu Arg His Lys Lys Gly
1               5                   10                  15

Thr Pro Val Gly Ile Tyr Ser Val Cys Ser Ala Asn Pro Phe Val Leu
            20                  25                  30

Lys Ala Ala Met Leu Gln Ala Gln Lys Asp Gln Ser Leu Leu Leu Ile
        35                  40                  45

```
Glu Ala Thr Ser Asn Gln Val Asp Gln Phe Gly Gly Tyr Thr Gly Met
    50                  55                  60
Arg Pro Glu Asp Phe Lys Thr Met Thr Leu Glu Leu Ala Ala Glu Asn
65                  70                  75                  80
Asn Tyr Asp Pro Gln Gly Leu Ile Leu Gly Gly Asp His Leu Gly Pro
                    85                  90                  95
Asn Arg Trp Thr Lys Leu Ser Ala Ser Arg Ala Met Asp Tyr Ala Arg
                100                 105                 110
Glu Gln Ile Ala Ala Tyr Val Lys Ala Gly Phe Ser Lys Ile His Leu
                115                 120                 125
Asp Ala Thr Met Pro Leu Gln Asn Asp Ala Thr Asp Ser Ala Gly Arg
            130                 135                 140
Leu Pro Val Glu Thr Ile Ala Gln Arg Thr Ala Glu Leu Cys Ala Val
145                 150                 155                 160
Ala Glu Gln Thr Tyr Arg Gln Ser Asp Gln Leu Phe Pro Pro Pro Val
                165                 170                 175
Tyr Ile Val Gly Ser Asp Val Pro Ile Pro Gly Gly Ala Gln Glu Ala
                180                 185                 190
Leu Asn Gln Ile His Ile Thr Glu Val Lys Glu Val Gln Thr Ile
            195                 200                 205
Asp His Val Arg Arg Ala Phe Glu Lys Asn Gly Leu Glu Ala Ala Tyr
            210                 215                 220
Glu Arg Val Cys Ala Val Val Gln Pro Gly Val Glu Phe Ala Asp
225                 230                 235                 240
Gln Ile Val Phe Glu Tyr Ala Pro Asp Arg Ala Ala Leu Lys Asp
                245                 250                 255
Phe Ile Glu Ser His Ser Gln Leu Val Tyr Glu Ala His Ser Thr Asp
                260                 265                 270
Tyr Gln Thr Ala Pro Leu Leu Arg Gln Met Val Lys Asp His Phe Ala
            275                 280                 285
Ile Leu Lys Val Gly Pro Ala Leu Thr Phe Ala Leu Arg Glu Ala Ile
            290                 295                 300
Phe Ala Leu Ala Phe Met Glu Lys Glu Leu Leu Pro Leu His Arg Ala
305                 310                 315                 320
Leu Lys Pro Ser Ala Ile Leu Glu Thr Leu Asp Gln Thr Met Asp Lys
                325                 330                 335
Asn Pro Ala Tyr Trp Gln Lys His Tyr Gly Gly Thr Lys Glu Glu Val
            340                 345                 350
Arg Phe Ala Gln Arg Phe Ser Leu Ser Asp Arg Ile Arg Tyr Tyr Trp
        355                 360                 365
Pro Phe Pro Lys Val Gln Lys Ala Leu Arg Gln Leu Leu Lys Asn Leu
    370                 375                 380
Gln Gln Ile Ser Ile Pro Leu Thr Leu Val Ser Gln Phe Met Pro Glu
385                 390                 395                 400
Glu Tyr Gln Arg Ile Arg Gln Gly Thr Leu Thr Asn Asp Pro Gln Ala
                405                 410                 415
Leu Ile Leu Asn Lys Ile Gln Ser Val Leu Lys Gln Tyr Ala Glu Ala
            420                 425                 430
Thr Gln Ile Gln Asn Ser Leu Thr Phe Thr Gln Asn Gln Asn Ser Leu
        435                 440                 445
Ala Met Glu Arg Leu
    450
```

<210> SEQ ID NO 9
<211> LENGTH: 1227
<212> TYPE: DNA
<213> ORGANISM: Dictyoglomus thermophilum

<400> SEQUENCE: 9

| | | | | | |
|---|---|---|---|---|---|
| atgtggctta | gtaaagatta | tttgagaaaa | aagggagttt | attctatatg | tagctctaat | 60 |
| ccatatgtga | ttgaggcaag | tgttgaattt | gctaaggaga | agaatgatta | tattttaatt | 120 |
| gaggcgacac | ctcatcagat | aaaccagttt | ggtggatatt | caggtatgac | tcccgaagat | 180 |
| tttaaaaact | tgtaatggg | aataataaaa | gaaaagggaa | tagaagagga | tagggtgatt | 240 |
| cttggagggg | accatttagg | ccctctccct | tggcaagatg | aaccttcttc | ttctgcaatg | 300 |
| aaaaaggcaa | aagaccttat | aagggccttt | gtggagagtg | gttataagaa | gatacacctt | 360 |
| gattgtagta | tgtctctttc | tgatgatcct | gtagtgctct | ctcccgagaa | gatagcagaa | 420 |
| agggagaggg | aacttcttga | ggttgcagaa | gagactgcta | gaaagtacaa | ttttcagcct | 480 |
| gtgtatgtgg | tgggaactga | tgtaccggta | gctggaggag | cgaagagga | aggtattacc | 540 |
| tcagtggagg | attttagagt | agcaatctcc | tcttttaaaaa | aatattttga | ggatgttcca | 600 |
| aggatatggg | ataggataat | tggttttgta | ataatgcttg | gtataggttt | taattatgaa | 660 |
| aaagtgtttg | agtatgacag | gattaaggtg | agaaaaattt | tagaggaggt | aaagaaagag | 720 |
| aatcttttg | ttgaaggtca | ctctactgac | tatcagacaa | aacgtgcatt | gagagatatg | 780 |
| gtagaggatg | gagtaagaat | tcttaaggtt | ggtcctgctt | taacagcaag | ttttagaagg | 840 |
| ggagtatttt | tattaagtag | cattgaggat | gagcttatat | cggaagataa | aaggtctaat | 900 |
| attaagaaag | ttgtgcttga | gactatgtta | aaagatgata | aatattggag | aaagtattat | 960 |
| aaggattcag | aaagattaga | attagatatt | tggtacaact | tacttgatag | gattagatat | 1020 |
| tattgggaat | ataaagagat | aaaaatagct | ttaaataggc | ttttttgaaaa | tttttcggaa | 1080 |
| ggggttgata | ttagatacat | ctatcaatat | ttttatgatt | cgtatttaa | agtaagagaa | 1140 |
| ggaaaaataa | gaaatgatcc | aagggagcta | ataagaatg | aaataaagaa | ggtcttggag | 1200 |
| gactatcact | atgctgtaaa | cttataa | | | | 1227 |

<210> SEQ ID NO 10
<211> LENGTH: 1227
<212> TYPE: DNA
<213> ORGANISM: Artificial Sequence
<220> FEATURE:
<223> OTHER INFORMATION: Codon optimized nucleotide sequence

<400> SEQUENCE: 10

| | | | | | |
|---|---|---|---|---|---|
| atgtggctga | gcaaggacta | cctgcgtaag | aagggcgttt | acagcatttg | cagcagcaac | 60 |
| ccgtatgtta | ttgaagcgag | cgtggagttc | gcgaaggaga | aaaacgatta | catcctgatt | 120 |
| gaagcgaccc | cgcaccagat | caaccaattt | ggtggctata | gcggcatgac | cccggaggac | 180 |
| ttcaagaact | tgttatggg | catcattaag | gaaaaaggta | tcgaggaaga | ccgtgtgatt | 240 |
| ctgggtggcg | atcacctggg | tccgctgccg | tggcaggatg | agccgagcag | cagcgcgatg | 300 |
| aagaaagcga | agaccctgat | ccgtgcgttc | gttgaaagcg | gttacaagaa | aattcacctg | 360 |
| gattgcagca | tgagcctgag | cgacgatccg | gtggttctga | gcccggagaa | gatcgcggaa | 420 |
| cgtgagcgtg | aactgctgga | agttgcggag | gaaaccgcgc | gtaaatacaa | ctttcaaccg | 480 |
| gtgtatgtgg | tgggtaccga | tgttccggtt | gcggtggcg | gtgaggaaga | gggtatcacc | 540 |
| agcgtggagg | acttccgtgt | tgcgattagc | agcctgaaga | aatactttga | agacgttccg | 600 |

```
cgtatttggg atcgtatcat tggtttcgtg atcatgctgg gcattggttt caactacgag      660
aaggtgtttg aatatgatcg tatcaaagtg cgtaaaattc tggaagaggt taagaaagag      720
aacctgtttg tggaaggcca cagcaccgac tatcagacca agcgtgcgct gcgtgacatg      780
gtggaggatg gcgttcgtat cctgaaagtg ggtccggcgc tgaccgcgag cttccgtcgt      840
ggtgtgtttc tgctgagcag catcgaggac gaactgatta gcgaggataa acgtagcaac      900
attaagaaag tggttctgga aaccatgctg aaggacgata atactggcg taagtactat       960 aaagacagcg agcgtctgga actggatatc tggtacaacc tgctggaccg tattcgttac     1020
tactgggagt acaaggaaat caagattgcg ctgaaccgtc tgttcgagaa ctttagcgaa     1080
ggcgttgata tccgttacat ctaccaatac ttctacgaca gctacttcaa agtgcgtgag     1140
ggtaaaatcc gtaacgaccc gcgtgaactg attaagaacg agattaagaa agtgctggaa     1200
gactaccatt atgcggtgaa cctgtaa                                         1227
```

<210> SEQ ID NO 11
<211> LENGTH: 408
<212> TYPE: PRT
<213> ORGANISM: Artificial Sequence
<220> FEATURE:
<223> OTHER INFORMATION: Codon optimized nucleotide sequence

<400> SEQUENCE: 11

```
Met Trp Leu Ser Lys Asp Tyr Leu Arg Lys Lys Gly Val Tyr Ser Ile
1               5                   10                  15

Cys Ser Ser Asn Pro Tyr Val Ile Glu Ala Ser Val Glu Phe Ala Lys
            20                  25                  30

Glu Lys Asn Asp Tyr Ile Leu Ile Glu Ala Thr Pro His Gln Ile Asn
        35                  40                  45

Gln Phe Gly Gly Tyr Ser Gly Met Thr Pro Glu Asp Phe Lys Asn Phe
    50                  55                  60

Val Met Gly Ile Ile Lys Glu Lys Gly Ile Glu Asp Arg Val Ile
65                  70                  75                  80

Leu Gly Gly Asp His Leu Gly Pro Leu Pro Trp Gln Asp Glu Pro Ser
                85                  90                  95

Ser Ser Ala Met Lys Lys Ala Lys Asp Leu Ile Arg Ala Phe Val Glu
            100                 105                 110

Ser Gly Tyr Lys Lys Ile His Leu Asp Cys Ser Met Ser Leu Ser Asp
        115                 120                 125

Asp Pro Val Val Leu Ser Pro Glu Lys Ile Ala Glu Arg Glu Arg Glu
    130                 135                 140

Leu Leu Glu Val Ala Glu Thr Ala Arg Lys Tyr Asn Phe Gln Pro
145                 150                 155                 160

Val Tyr Val Val Gly Thr Asp Val Pro Val Ala Gly Gly Glu Glu
                165                 170                 175

Glu Gly Ile Thr Ser Val Glu Asp Phe Arg Val Ala Ile Ser Ser Leu
            180                 185                 190

Lys Lys Tyr Phe Glu Asp Val Pro Arg Ile Trp Asp Arg Ile Ile Gly
        195                 200                 205

Phe Val Ile Met Leu Gly Ile Gly Phe Asn Tyr Glu Lys Val Phe Glu
    210                 215                 220

Tyr Asp Arg Ile Lys Val Arg Lys Ile Leu Glu Glu Val Lys Lys Glu
225                 230                 235                 240

Asn Leu Phe Val Glu Gly His Ser Thr Asp Tyr Gln Thr Lys Arg Ala
```

```
                         245                 250                 255
Leu Arg Asp Met Val Glu Asp Gly Val Arg Ile Leu Lys Val Gly Pro
            260                 265                 270

Ala Leu Thr Ala Ser Phe Arg Arg Gly Val Phe Leu Leu Ser Ser Ile
            275                 280                 285

Glu Asp Glu Leu Ile Ser Glu Asp Lys Arg Ser Asn Ile Lys Lys Val
            290                 295                 300

Val Leu Glu Thr Met Leu Lys Asp Asp Lys Tyr Trp Arg Lys Tyr Tyr
305                 310                 315                 320

Lys Asp Ser Glu Arg Leu Glu Leu Asp Ile Trp Tyr Asn Leu Leu Asp
                325                 330                 335

Arg Ile Arg Tyr Tyr Trp Glu Tyr Lys Glu Ile Lys Ile Ala Leu Asn
            340                 345                 350

Arg Leu Phe Glu Asn Phe Ser Glu Gly Val Asp Ile Arg Tyr Ile Tyr
            355                 360                 365

Gln Tyr Phe Tyr Asp Ser Tyr Phe Lys Val Arg Glu Gly Lys Ile Arg
            370                 375                 380

Asn Asp Pro Arg Glu Leu Ile Lys Asn Glu Ile Lys Lys Val Leu Glu
385                 390                 395                 400

Asp Tyr His Tyr Ala Val Asn Leu
            405

<210> SEQ ID NO 12
<211> LENGTH: 672
<212> TYPE: DNA
<213> ORGANISM: Archaeoglobus fulgidus

<400> SEQUENCE: 12
atgttcaaac caaaggccat cgcagttgac atagatggca ccctcaccga cagaaagagg      60
gctctgaact gcagggctgt tgaagctctc cgcaaggtaa aaattcccgt gattttggcc     120
actggtaaca tatcttgttt tgcgagggct gcagcaaagc tgattggagt ctcagacgtg     180
gtaatctgcg agaatggggg cgtggtgagg ttcgagtacg atggggagga tattgtttta     240
ggagataaag agaaatgcgt tgaggctgtg agggtgcttg agaaacacta tgaggttgag     300
ctgctggact tcgaatacag gaagtcggaa gtgtgcatga ggaggagctt tgacatcaac     360
gaggcgagaa agctcattga ggggatgggg gttaagcttg tggattcagg ctttgcctac     420
cacattatgg atgctgatgt tagcaaggga aaagctttga agttcgttgc cgagaggctt     480
ggtatcagtt cagcggagtt tgcagttatc ggcgactcag agaacgacat agacatgttc     540
agagttgctg gattcggaat tgctgttgcc aatgccgatg agaggctgaa ggagtatgct     600
gatttagtta cgccatcacc agacggcgag ggggttgttg aggctttgca gtttctggga     660
ttgttgcggt ga                                                          672

<210> SEQ ID NO 13
<211> LENGTH: 223
<212> TYPE: PRT
<213> ORGANISM: Archaeoglobus fulgidus

<400> SEQUENCE: 13

Met Phe Lys Pro Lys Ala Ile Ala Val Asp Ile Asp Gly Thr Leu Thr
1               5                   10                  15

Asp Arg Lys Arg Ala Leu Asn Cys Arg Ala Val Glu Ala Leu Arg Lys
            20                  25                  30

Val Lys Ile Pro Val Ile Leu Ala Thr Gly Asn Ile Ser Cys Phe Ala
```

```
            35                  40                  45
Arg Ala Ala Lys Leu Ile Gly Val Ser Asp Val Val Ile Cys Glu
 50                  55                  60

Asn Gly Gly Val Val Arg Phe Glu Tyr Asp Gly Glu Asp Ile Val Leu
 65                  70                  75                  80

Gly Asp Lys Glu Lys Cys Val Glu Ala Val Arg Val Leu Glu Lys His
                 85                  90                  95

Tyr Glu Val Glu Leu Leu Asp Phe Glu Tyr Arg Lys Ser Glu Val Cys
             100                 105                 110

Met Arg Arg Ser Phe Asp Ile Asn Glu Ala Arg Lys Leu Ile Glu Gly
         115                 120                 125

Met Gly Val Lys Leu Val Asp Ser Gly Phe Ala Tyr His Ile Met Asp
     130                 135                 140

Ala Asp Val Ser Lys Gly Lys Ala Leu Lys Phe Val Ala Glu Arg Leu
145                 150                 155                 160

Gly Ile Ser Ser Ala Glu Phe Ala Val Ile Gly Asp Ser Glu Asn Asp
                165                 170                 175

Ile Asp Met Phe Arg Val Ala Gly Phe Gly Ile Ala Val Ala Asn Ala
            180                 185                 190

Asp Glu Arg Leu Lys Glu Tyr Ala Asp Leu Val Thr Pro Ser Pro Asp
        195                 200                 205

Gly Glu Gly Val Val Glu Ala Leu Gln Phe Leu Gly Leu Leu Arg
    210                 215                 220

<210> SEQ ID NO 14
<211> LENGTH: 660
<212> TYPE: DNA
<213> ORGANISM: Archaeoglobus profundus

<400> SEQUENCE: 14
gtgttcaagg ctttggtagt tgatatagac ggaactttga cggataagaa gagggcaata      60
aactgcagag cggtcgaagc acttagaaaa ctaaagattc ctgttgtctt ggcaaccgga     120
aacatttcat gctttgcaag ggctgtagct aagattatag gtgtttccga tattgtaata     180
gctgagaacg gaggtgttgt cagattcagc tacgacggag aggacatagt tctgggggat     240
agaagtaaat gcttaagagc tttggagaca cttagaaaac gcttcaaagt agagcttctc     300
gacaacgaat ataggaagtc tgaggtctgc atgaggagga cttcccctat agaggaagct     360
agaaagatac tgccaaaaga tgttagaata gtcgatacag gcttcgcata ccacataatc     420
gatgcaaatg tcagcaaggg gaaggctttg atgttcatag ccgataagct tggcttggac     480
gttaaggatt tcattgcgat aggtgattcc gaaaacgaca ttgaaatgtt ggaagttgca     540
ggttttggcg ttgcagttgc gaatgcggat gaaaagctta aggaggtagc ggatttggtc     600
acatcgaagc ctaatggaga cggagttgtc gaagctcttg agttcttggg actcatttag     660

<210> SEQ ID NO 15
<211> LENGTH: 219
<212> TYPE: PRT
<213> ORGANISM: Archaeoglobus profundus

<400> SEQUENCE: 15

Met Phe Lys Ala Leu Val Val Asp Ile Asp Gly Thr Leu Thr Asp Lys
  1               5                  10                  15

Lys Arg Ala Ile Asn Cys Arg Ala Val Glu Ala Leu Arg Lys Leu Lys
             20                  25                  30
```

Ile Pro Val Val Leu Ala Thr Gly Asn Ile Ser Cys Phe Ala Arg Ala
         35                  40                  45

Val Ala Lys Ile Ile Gly Val Ser Asp Ile Val Ile Ala Glu Asn Gly
     50                  55                  60

Gly Val Val Arg Phe Ser Tyr Asp Gly Glu Asp Ile Val Leu Gly Asp
 65                  70                  75                  80

Arg Ser Lys Cys Leu Arg Ala Leu Glu Thr Leu Arg Lys Arg Phe Lys
                 85                  90                  95

Val Glu Leu Leu Asp Asn Glu Tyr Arg Lys Ser Glu Val Cys Met Arg
            100                 105                 110

Arg Asn Phe Pro Ile Glu Glu Ala Arg Lys Ile Leu Pro Lys Asp Val
        115                 120                 125

Arg Ile Val Asp Thr Gly Phe Ala Tyr His Ile Ile Asp Ala Asn Val
    130                 135                 140

Ser Lys Gly Lys Ala Leu Met Phe Ile Ala Asp Lys Leu Gly Leu Asp
145                 150                 155                 160

Val Lys Asp Phe Ile Ala Ile Gly Asp Ser Glu Asn Asp Ile Glu Met
                165                 170                 175

Leu Glu Val Ala Gly Phe Gly Val Ala Val Ala Asn Ala Asp Glu Lys
            180                 185                 190

Leu Lys Glu Val Ala Asp Leu Val Thr Ser Lys Pro Asn Gly Asp Gly
        195                 200                 205

Val Val Glu Ala Leu Glu Phe Leu Gly Leu Ile
    210                 215

<210> SEQ ID NO 16
<211> LENGTH: 675
<212> TYPE: DNA
<213> ORGANISM: Archaeoglobus veneficus

<400> SEQUENCE: 16
atgctccgtc caaagggtct cgccattgac atcgacggaa ccataacata caggaatcga     60
agcctgaact gtaaggccgt tgaagctctc aggaaggtaa aaatccctgt agttcttgca    120
actggcaaca tatcctgttt cgcaagaact gctgcaaagc ttataggcgt ctcagacatt    180
gttatatgcg aaaatggagg tattgttcga ttcagctacg atggcgacga catagtgctt    240
ggggacataa gcaaatgcct taaagcggct gaaattctca agagtacttt gaaatcgaa    300
ttccttgacg ctgagtacag gaagtcggag gtctgtcttc gcagaaactt cctattgaa    360
gaggcgagga aaattcttca cgatgcaaag cttgatgtta aaatcgtcga ttcaggtttt    420
gcgtaccaca taatggatgc gaaggtcagc aaaggaaggg ctcttgagta catagctgat    480
gaacttggta aagtccgaa ggagttcgct gcaattggtg attctgagaa cgacatagac    540
ctgattaagg ctgccggcct cggtattgcc gttggagatg ctgacttaaa gctcaaaatg    600
gaggccgacg tggtagtctc gaagaagaat ggcgatggag ttgttgaagc acttgagctt    660
ctgggcttaa tttaa                                                     675

<210> SEQ ID NO 17
<211> LENGTH: 224
<212> TYPE: PRT
<213> ORGANISM: Archaeoglobus veneficus

<400> SEQUENCE: 17

Met Leu Arg Pro Lys Gly Leu Ala Ile Asp Ile Asp Gly Thr Ile Thr
 1               5                  10                  15

-continued

```
Tyr Arg Asn Arg Ser Leu Asn Cys Lys Ala Val Glu Ala Leu Arg Lys
            20                  25                  30

Val Lys Ile Pro Val Val Leu Ala Thr Gly Asn Ile Ser Cys Phe Ala
        35                  40                  45

Arg Thr Ala Ala Lys Leu Ile Gly Val Ser Asp Ile Val Ile Cys Glu
    50                  55                  60

Asn Gly Gly Ile Val Arg Phe Ser Tyr Asp Gly Asp Asp Ile Val Leu
65                      70                  75                  80

Gly Asp Ile Ser Lys Cys Leu Lys Ala Ala Glu Ile Leu Lys Glu Tyr
                85                  90                  95

Phe Glu Ile Glu Phe Leu Asp Ala Glu Tyr Arg Lys Ser Glu Val Cys
            100                 105                 110

Leu Arg Arg Asn Phe Pro Ile Glu Glu Ala Arg Lys Ile Leu His Asp
        115                 120                 125

Ala Lys Leu Asp Val Lys Ile Val Asp Ser Gly Phe Ala Tyr His Ile
    130                 135                 140

Met Asp Ala Lys Val Ser Lys Gly Arg Ala Leu Glu Tyr Ile Ala Asp
145                 150                 155                 160

Glu Leu Gly Ile Ser Pro Lys Glu Phe Ala Ala Ile Gly Asp Ser Glu
                165                 170                 175

Asn Asp Ile Asp Leu Ile Lys Ala Ala Gly Leu Gly Ile Ala Val Gly
            180                 185                 190

Asp Ala Asp Leu Lys Leu Lys Met Glu Ala Asp Val Val Val Ser Lys
        195                 200                 205

Lys Asn Gly Asp Gly Val Val Glu Ala Leu Glu Leu Leu Gly Leu Ile
210                 215                 220
```

ENZYMATIC PRODUCTION OF D-TAGATOSE

CROSS-REFERENCE TO RELATED APPLICATIONS

This application is a Continuation of U.S. application Ser. No. 16/145,887, filed Sep. 28, 2018; which claims priority to U.S. application Ser. No. 15/743,481, filed Jan. 10, 2018; which claims priority to PCT International Application No. PCT/US2016/054838 filed Sep. 30, 2016; and to U.S. Provisional Application No. 62/236,226, filed Oct. 2, 2015, which is incorporated herein by reference.

SEQUENCE LISTING

The Sequence Listing submitted herewith is an ASCII text file (2020-01-07_Sequence_Listing.text, created on Jan. 7, 2020, 38,473 bytes) via EFS-Web is hereby incorporated by reference.

FIELD OF THE INVENTION

The invention relates to preparation of the sugar D-tagatose. More specifically, the invention relates to methods of preparing D-tagatose by enzymatically converting saccharides (e.g., polysaccharides, oligosaccharides, disaccharides, sucrose, D-glucose, and D-fructose) into D-tagatose.

BACKGROUND OF THE INVENTION

D-tagatose (tagatose hereafter) is a low-calorie, natural sweetener that has 92% the sweetness of sucrose, but only 38% of the calories. It is a naturally occurring monosaccharide hexose that is present in only small amounts in fruits, cacao, and dairy products. Tagatose was approved as a food additive by the Food and Drug Administration (FDA) in 2003, which designated it as generally recognized as safe (GRAS). However, due to tagatose's high selling prices, its use as a sweetener has been limited. Tagatose boasts a myriad of health benefits: it is non-cariogenic; it is low-calorie; it has a very low glycemic index of 3; it attenuates the glycemic index of glucose by 20%; it can lower average blood glucose levels; it helps prevent cardiovascular disease, strokes, and other vascular diseases by raising high-density lipoprotein (HDL) cholesterol; and it is a verified prebiotic and antioxidant. Lu et al., Tagatose, a New Antidiabetic and Obesity Control Drug, Diabetes Obes. Metab. 10(2): 109-34 (2008). As such, tagatose clearly has a variety of applications in the pharmaceutical, biotechnological, academic, food, beverage, dietary supplement, and grocer industries.

Currently tagatose is produced predominantly through the hydrolysis of lactose by lactase or acid hydrolysis to form D-glucose and D-galactose (WO 2011150556, CN 103025894, U.S. Pat. Nos. 5,002,612, 6,057,135, and 8,802, 843). The D-galactose is then isomerized to D-tagatose either chemically by calcium hydroxide under alkaline conditions or enzymatically by L-arabinose isomerase under pH neutral conditions. The final product is isolated by a combination of filtration and ion exchange chromatography. This process is performed in several tanks or bioreactors. Overall, the method suffers because of the costly separation of other sugars (e.g., D-glucose, D-galactose, and unhydrolyzed lactose) and low product yields. Several methods via microbial cell fermentation are being developed, but none have been proven to be a practical alternative due to their dependence on costly feedstock (e.g., galactitol and D-psicose), low product yields, and costly separation.

There is a need to develop a cost-effective synthetic pathway for high-yield tagatose production where at least one step of the process involves an energetically favorable chemical reaction. Furthermore, there is a need for a tagatose production process where the process steps can be conducted in one tank or bioreactor. There is also a need for a process of tagatose production that can be conducted at a relatively low concentration of phosphate, where phosphate can be recycled, and/or the process does not require using adenosine triphosphate (ATP) as a source of phosphate. There is also a need for a tagatose production pathway that does not require the use of the costly nicotinamide adenosine dinucleotide (NAD(H)) coenzyme in any of the reaction steps.

SUMMARY OF THE INVENTION

The inventions described herein relate to processes for preparing tagatose. In various aspects, the processes involve converting fructose 6-phosphate (F6P) to tagatose 6-phosphate (T6P), catalyzed by an epimerase; and converting the T6P to tagatose, catalyzed by a phosphatase. The inventions also relate to tagatose prepared by any of the processes described herein.

In some aspects of the invention, a process for preparing tagatose also involves the step of converting glucose 6-phosphate (G6P) to the F6P, where the step is catalyzed by phosphoglucose isomerase (PGI). In other aspects, a process for tagatose synthesis also includes the step of converting glucose 1-phosphate (G1P) to the G6P, and this conversion step is catalyzed by phosphoglucomutase (PGM).

In various aspects, a process for preparing tagatose can involve converting a saccharide to the G1P, catalyzed by at least one enzyme; converting G1P to G6P, catalyzed by phosphoglucomutase (PGM); converting G6P to F6P, catalyzed by phosphoglucose isomerase (PGI); converting F6P to tagatose 6-phosphate (T6P), catalyzed by an epimerase; and converting the T6P produced to tagatose, catalyzed by a phosphatase.

The saccharides used in any of the processes can be selected from the group consisting of a starch or its derivative, cellulose or its derivative, and sucrose. The starch or its derivative can be amylose, amylopectin, soluble starch, amylodextrin, maltodextrin, maltose, or glucose. In some aspects of the invention, a process for preparing tagatose involves converting starch to a starch derivative by enzymatic hydrolysis or by acid hydrolysis of starch. In other aspects, a starch derivative can be is prepared by enzymatic hydrolysis of starch catalyzed by isoamylase, pullulanase, alpha-amylase, or a combination of two or more of these enzymes. A process for preparing tagatose, in certain aspects, can also involve adding 4-glucan transferase (4GT).

In various aspects, a process for preparing tagatose can involve converting fructose to the F6P, catalyzed by at least one enzyme; converting F6P to tagatose 6-phosphate (T6P) catalyzed by an epimerase; and converting the T6P produced to tagatose, catalyzed by a phosphatase. In other embodiments, a tagatose production process involves converting sucrose to the fructose, catalyzed by at least one enzyme; converting fructose to the F6P, catalyzed by at least one enzyme; converting F6P to tagatose 6-phosphate (T6P) catalyzed by an epimerase; and converting the T6P produced to tagatose, catalyzed by a phosphatase.

In other aspects of the invention, G6P to be used in a process for preparing tagatose can be generated by converting glucose to the G6P, catalyzed by at least one enzyme. Glucose can in turn be produced by converting sucrose to glucose, catalyzed by at least one enzyme.

In some aspects of the invention, epimerase used to convert F6P to T6P is fructose 6-phosphate epimerase. The fructose 6-phosphate epimerase can be encoded by a polynucleotide comprising a nucleotide sequence having at least 60%, at least 70%, at least 80%, at least 85%, at least 90%, at least 95%, at least 97%, at least 99%, or 100% sequence identity with SEQ ID NOS.: 1, 3, 5, 7, 9, or 10. In various aspects, the fructose 6-phosphate epimerase comprises an amino acid sequence having at least 60%, at least 70%, at least 80%, at least 85%, at least 90%, at least 95%, at least 97%, at least 99%, or 100% sequence identity with SEQ ID NOS.: 2, 4, 6, 8, or 11.

In various aspects of the invention, the phosphatase used to convert T6P to tagatose is tagatose 6-phosphate phosphatase. The tagatose 6-phosphate phosphatase can be encoded by a polynucleotide comprising a nucleotide sequence having at least 60%, at least 70%, at least 80%, at least 85%, at least 90%, at least 95%, at least 97%, at least 99%, or 100% sequence identity with SEQ ID NO.: 12, 14, or 16. In some aspects of the invention, the tagatose 6-phosphate phosphatase comprises an amino acid sequence having at least 60%, at least 70%, at least 80%, at least 85%, at least 90%, at least 95%, at least 97%, at least 99%, or 100% sequence identity with SEQ ID NO.: 13, 15, or 17.

In various aspects, a process of the invention are be conducted at a temperature ranging from about 40° C. to about 70° C., at a pH ranging from about 5.0 to about 8.0, and/or for about 8 hours to about 48 hours. In some aspects, the steps of a process for preparing tagatose are conducted in one bioreactor. In other aspects, the steps are conducted in a plurality of bioreactors arranged in series.

In other aspects of the invention, the steps of a process for preparing tagatose are conducted ATP-free, NAD(H)-free, at a phosphate concentration from about 0 mM to about 150 mM, the phosphate is recycled, and/or at least one step of the process involves an energetically favorable chemical reaction.

BRIEF DESCRIPTION OF THE FIGURES

These drawings illustrate certain aspects of some of the embodiments of the invention, and should not be used to limit or define the invention.

DETAILED DESCRIPTION OF THE INVENTION

The invention provides enzymatic pathways, or processes, for synthesizing tagatose with a high product yield, while greatly decreasing the product separation costs and tagatose production costs.

Figure 1:
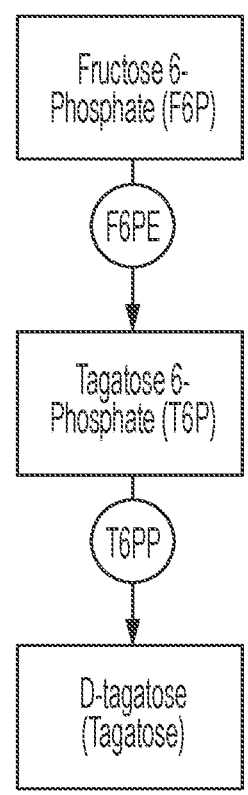
FIG. 1 is a schematic diagram illustrating an enzymatic pathway converting fructose 6-phosphate to tagatose 6-phosphate and then to D-tagatose (tagatose).

The invention relates to a process for preparing tagatose where the process involves converting fructose 6-phosphate (F6P) to tagatose 6-phosphate (T6P) catalyzed by an epimerase and converting the T6P produced to tagatose catalyzed by a phosphatase (e.g., tagatose 6-phosphate phosphatase, T6PP). This process is generally shown in FIG. 1. In certain embodiments, the epimerase that catalyzes the conversion of F6P to T6P is fructose 6-phosphate epimerase (F6PE).

Epimerases that convert F6P to T6P may be used in a process of the invention. In some aspects of the invention, epimerases suitable for use in the processes to convert F6P to T6P comprise an amino acid sequence that has a degree of identity to the amino acid sequence of SEQ ID NOS.: 2, 4, 6, 8, or 11 (shown below), of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%. The suitable epimerases are encoded by a polynucleotide comprising a nucleotide sequence that has a degree of identity to the nucleotide sequence of SEQ ID NOS.: 1, 3, 5, 7, 9, or 10 (shown below), of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%.

The invention also relates to epimerases that comprise an amino acid sequence that has a degree of identity to the amino acid sequence of SEQ ID NOS.: 2, 4, 6, 8, or 11, of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%. In other aspects, the invention relates to epimerases that are encoded by a polynucleotide comprising a nucleotide sequence that has a degree of identity to the nucleotide sequence of SEQ ID NOS.: 1, 3, 5, 7, 9, or 10, of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%.

Phosphatases that convert T6P to tagatose (D-tagatose) may be used in a process of the invention. In some aspects of the invention, phosphatases that can be used in to convert T6P to tagatose (D-tagatose) comprise an amino acid sequence that has a degree of identity to the amino acid sequence of SEQ ID NOS.: 12, 14, or 16 (shown below), of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%. The tagatose phosphatases are encoded by a polynucleotide comprising a nucleotide sequence that has a degree of identity to the nucleotide sequence of SEQ ID NOS.: 13, 15, or 17 (shown below), of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%.

The invention also relates to phosphatases that convert T6P to tagatose (D-tagatose) and comprise an amino acid sequence that has a degree of identity to the amino acid sequence of SEQ ID NOS.: 12, 14, or 16, of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%. In various aspects, the invention relates to phosphatases that convert T6P to tagatose (D-tagatose) and are encoded by a polynucleotide comprising a nucleotide sequence that has a degree of identity to the nucleotide sequence of SEQ ID NOS.: 13, 15, or 17, of at least 60%, preferably at least 65%, more preferably at least 70%, more preferably at least 75%, more preferably at least 80%, more preferably at least 85%, even more preferably at least 90%, most preferably at least 95%, and even most preferably at least 96%, 97%, 98%, 99%, or 100%.

In some embodiments, a process for preparing tagatose according to the invention also includes the step of enzymatically converting glucose 6-phosphate (G6P) to the F6P, and this step is catalyzed by phosphoglucose isomerase (PGI). In other embodiments, the process for preparing tagatose additionally includes the step of converting glucose 1-phosphate (G1P) to the G6P, where the step is catalyzed by phosphoglucomutase (PGM). In yet further embodiments, tagatose production process also includes the step of converting a saccharide to the G1P that is catalyzed at least one enzyme.

Figure 2:
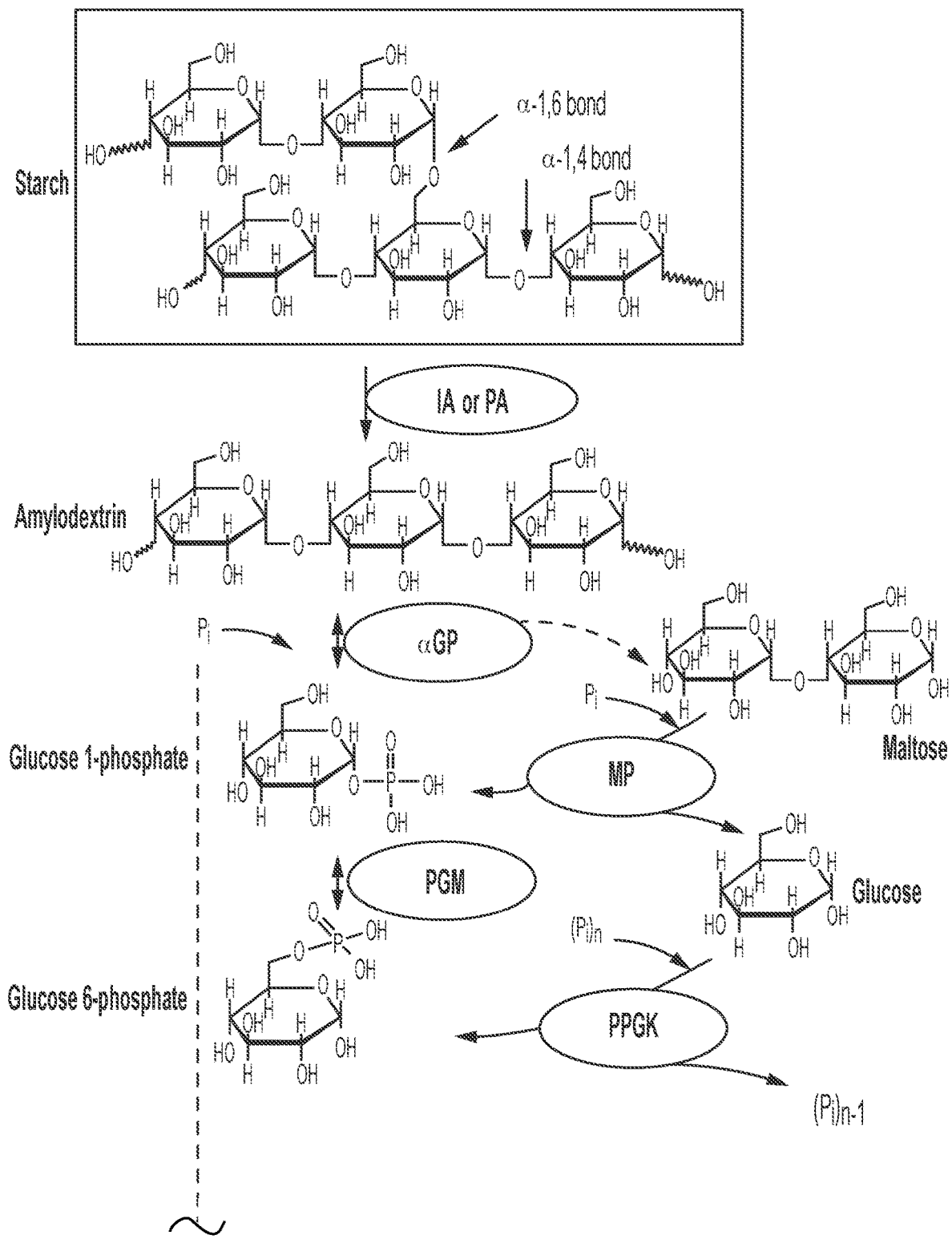
FIG. 2 is a schematic diagram illustrating an enzymatic pathway converting starch or its derived products to tagatose. The following abbreviations are used: αGP, alpha-glucan phosphorylase or starch phosphorylase; PGM, phosphoglucomutase; PGI, phosphoglucoisomerase; F6PE, fructose 6-phosphate epimerase; T6PP, tagatose 6-phosphate phosphatase; IA, isoamylase; PA, pullulanase; MP, maltose phosphorylase; PPGK, polyphosphate glucokinase.
Figure 2:
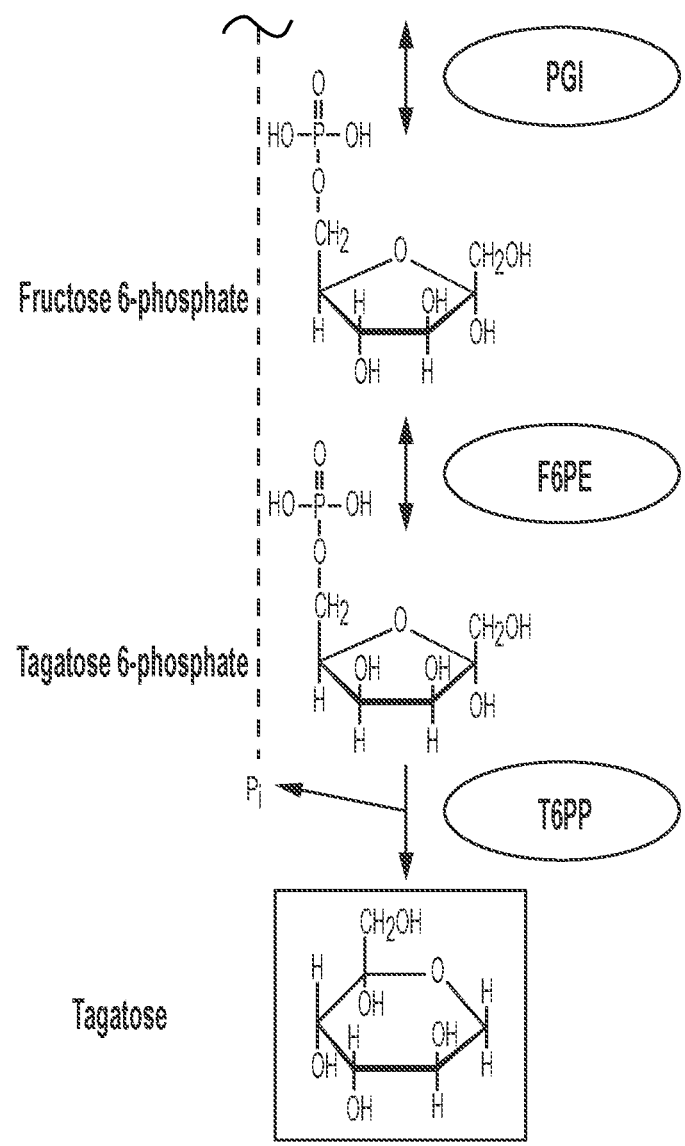

Therefore, a process for preparing tagatose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via fructose 6-phosphate epimerase (F6PE), and (v) converting T6P to tagatose via tagatose 6-phosphate phosphatase (T6PP). An example of the process where the saccharide is starch is shown in FIG. 2.

Typically, the ratios of enzyme units used in the disclosed process are 1:1:1:1:1 (αGP:PGM:PGI:F6PE:T6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:3 can be used to further increase the reaction rate. Therefore, the enzyme ratios, including other optional enzymes discussed below, can be varied to increase the efficiency of tagatose production. For example, a particular enzyme may be present in an amount about 2×, 3×, 4×, 5×, etc. relative to the amount of other enzymes.

One of the important advantages of the processes is that the process steps can be conducted in one bioreactor or reaction vessel. Alternatively, the steps can also be conducted in a plurality of bioreactors, or reaction vessels, that are arranged in series.

Phosphate ions produced by T6PP dephosphorylation of T6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the tagatose making processes.

For example, reaction phosphate concentrations can range from about 0 mM to about 300 mM, from about 0 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of T6PP by high concentrations of free phosphate and decreases the potential for phosphate pollution.

Figure 7:
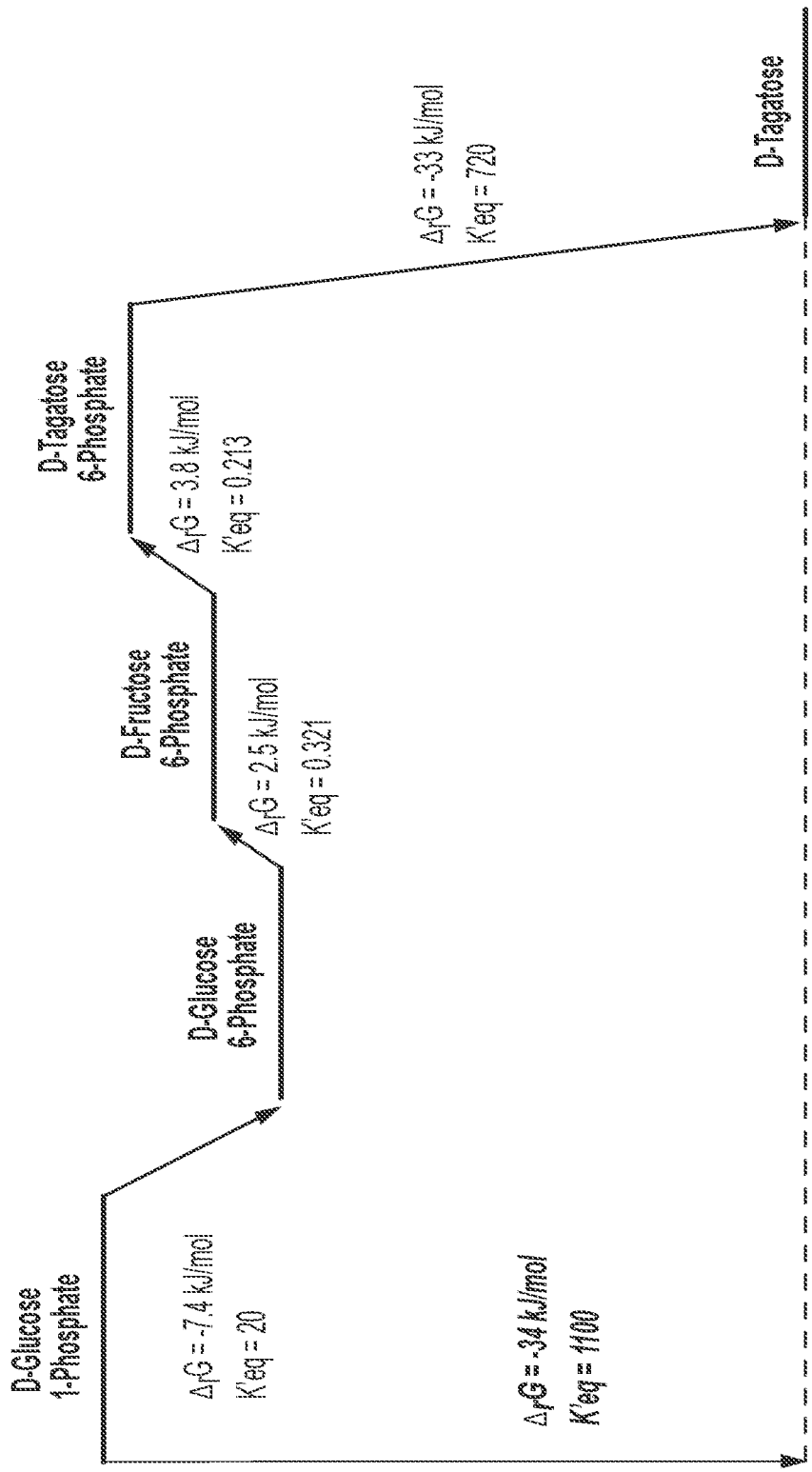
FIG. 7 shows the Reaction Gibbs Energy between intermediates based on formation Gibbs energy for the conversion of glucose 1-phosphate to tagatose.

Furthermore, the processes disclosed herein can be conducted without added ATP as a source of phosphate, i.e., ATP-free. The processes can also be conducted without having to add NAD(H), i.e., NAD(H)-free. Other advantages also include the fact that at least one step of the disclosed processes for making tagatose involves an energetically favorable chemical reaction (FIG. 7).

Examples of the enzymes used to convert a saccharide to G1P include alpha-glucan phosphorylase (αGP, EC 2.4.1.1), maltose phosphorylase (MP, EC 2.4.1.8), cellodextrin phosphorylase (CDP, EC 2.4.1.49), cellobiose phosphorylase (CBP, EC 2.4.1.20), cellulose phosphorylase, sucrose phosphorylase (SP, EC 2.4.1.7), and a combination thereof. The choice of the enzyme or enzyme combination depends on the saccharide used in the process.

The saccharides used for generating G1P can be polysaccharides, oligosaccharides, and/or disaccharides. For example, the saccharide can be starch, one or more derivatives of starch, cellulose, one or more derivatives of cellulose, sucrose, one or more derivatives of sucrose, or a combination thereof.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

The derivatives of starch can be prepared by enzymatic hydrolysis of starch or by acid hydrolysis of starch. Specifically, the enzymatic hydrolysis of starch can be catalyzed or enhanced by isoamylase (IA, EC. 3.2.1.68), which hydrolyzes α-1,6-glucosidic bonds; pullulanase (PA, EC. 3.2.1.41), which hydrolyzes α-1,6-glucosidic bonds; 4-α-glucanotransferase (4GT, EC. 2.4.1.25), which catalyzes the transglycosylation of short maltooligosaccharides, yielding longer maltooligosaccharides; or alpha-amylase (EC 3.2.1.1), which cleaves α-1,4-glucosidic bonds.

Furthermore, derivatives of cellulose can be prepared by enzymatic hydrolysis of cellulose catalyzed by cellulase mixtures, by acids, or by pretreatment of biomass.

In certain embodiments, the enzymes used to convert a saccharide to G1P contain αGP. In this step, when the saccharides include starch, the G1P is generated from starch by αGP; when the saccharides contain soluble starch, amylodextrin, or maltodextrin, the G1P is produced from soluble starch, amylodextrin, or maltodextrin by αGP.

When the saccharides include maltose and the enzymes contain maltose phosphorylase, the G1P is generated from maltose by maltose phosphorylase. If the saccharides include sucrose, and enzymes contain sucrose phosphorylase, the G1P is generated from sucrose by sucrose phosphorylase.

In yet another embodiment, when the saccharides include cellobiose, and the enzymes contain cellobiose phosphorylase, the G1P is generated from cellobiose by cellobiose phosphorylase.

In an additional embodiment, when the saccharides contain cellodextrins and the enzymes include cellodextrin phosphorylase, the G1P is generated from cellodextrins by cellodextrin phosphorylase.

In an alternative embodiment of converting a saccharide to G1P, when the saccharides include cellulose, and enzymes contain cellulose phosphorylase, the G1P is generated from cellulose by cellulose phosphorylase.

Figure 4:
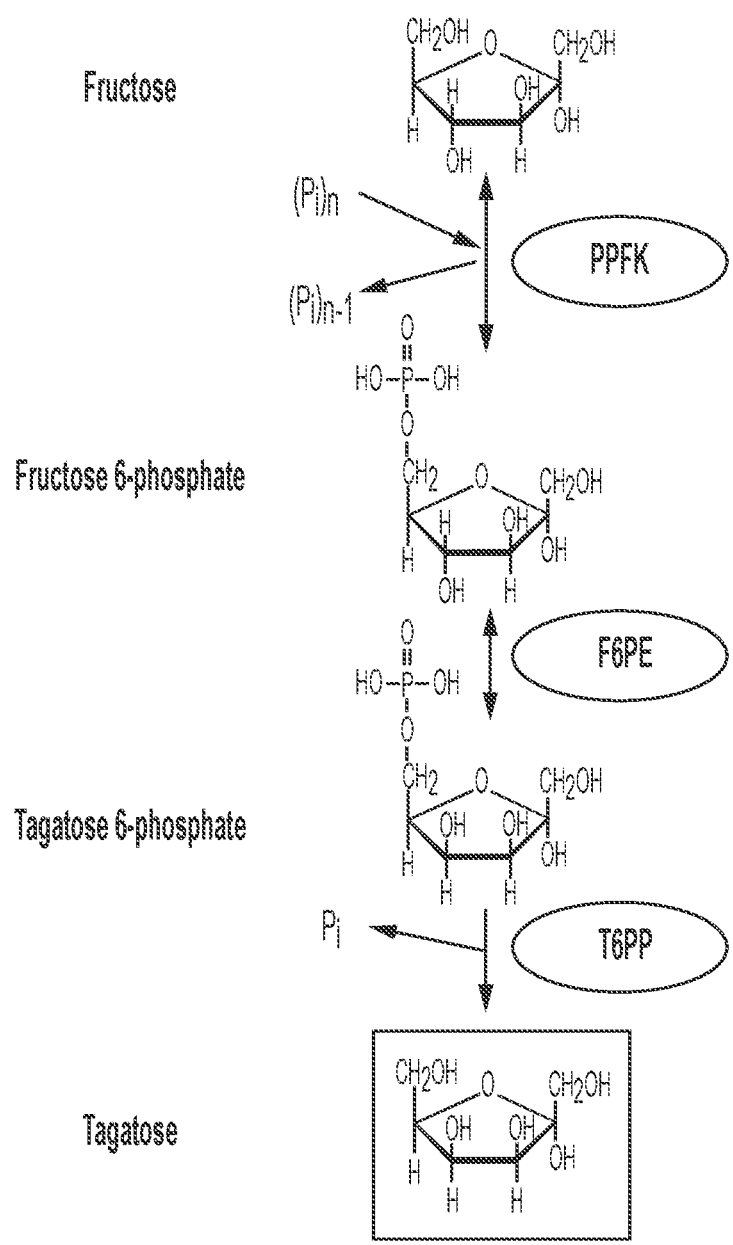
FIG. 4 is a schematic diagram illustrating an enzymatic pathway converting fructose to tagatose. PPFK, polyphosphate fructokinase; F6PE, fructose 6-phosphate epimerase; T6PP, tagatose 6-phosphate phosphatase.

According to the invention, tagatose can also be produced from fructose. An example of the process is shown in FIG. 4. For example, the process involves generating F6P from fructose and polyphosphate catalyzed by polyphosphate fructokinase (PPFK); converting F6P to T6P catalyzed by F6PE; and converting T6P to tagatose catalyzed by T6PP. The fructose can be produced, for example, by an enzymatic conversion of sucrose.

Figure 6:
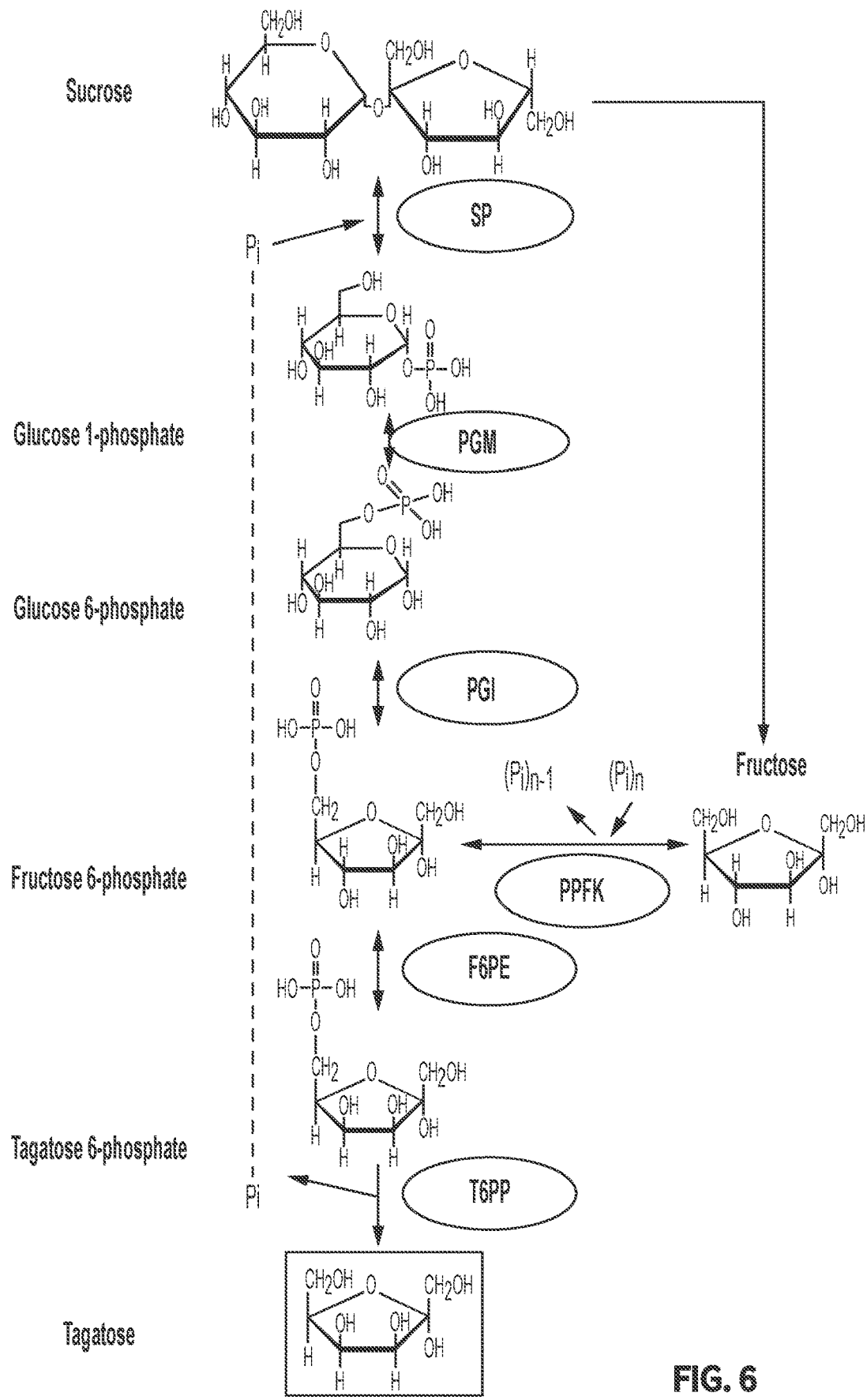
FIG. 6 shows an enzymatic pathway converting sucrose or its derived products to tagatose. SP, sucrose phosphorylase; PPFK, polyphosphate fructokinase ; PGM, phosphoglucomutase; PGI, phosphoglucoisomerase; F6PE, fructose 6-phosphate epimerase; T6PP, tagatose 6-phosphate phosphatase.

In other embodiments, tagatose can be produced from sucrose. An example of such process is shown in FIG.6. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; and converting T6P to tagatose catalyzed by T6PP.

The phosphate ions generated when T6P is converted to tagatose can then be recycled in the step of converting sucrose to G1P. Additionally, as shown in FIG. 6, PPFK and polyphosphate can be used to increase tagatose yields by producing F6P from fructose generated by the phosphorolytic cleavage of sucrose by SP.

In some embodiments, a process for preparing tagatose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to tagatose. In certain embodiments, artificial (non-natural) ATP-free enzymatic pathways are provided to convert starch, cellulose, sucrose, and their derived products to tagatose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to tagatose.

As shown in FIG. 2, maltose phosphorylase (MP) can be used to increase tagatose yields by phosphorolytically cleaving the degradation product maltose into G1P and glucose. Alternatively, 4-glucan transferase (4GT) can be used to increase tagatose yields by recycling the degradation products glucose, maltose, and maltotriose into longer maltooligosaccharides; which can be phosphorolytically cleaved by αGP to yield G1P.

Additionally, cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

In certain embodiments, cellulose and its derived products can be converted to tagatose through a series of steps. An example of such process is a shown in FIG. 3. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; and converting T6P to tagatose catalyzed by T6PP. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partially hydrolyzed by using concentrated acids, including hydrochloric acid, sulfuric acid, phosphoric acid and their combinations.

Figure 3:
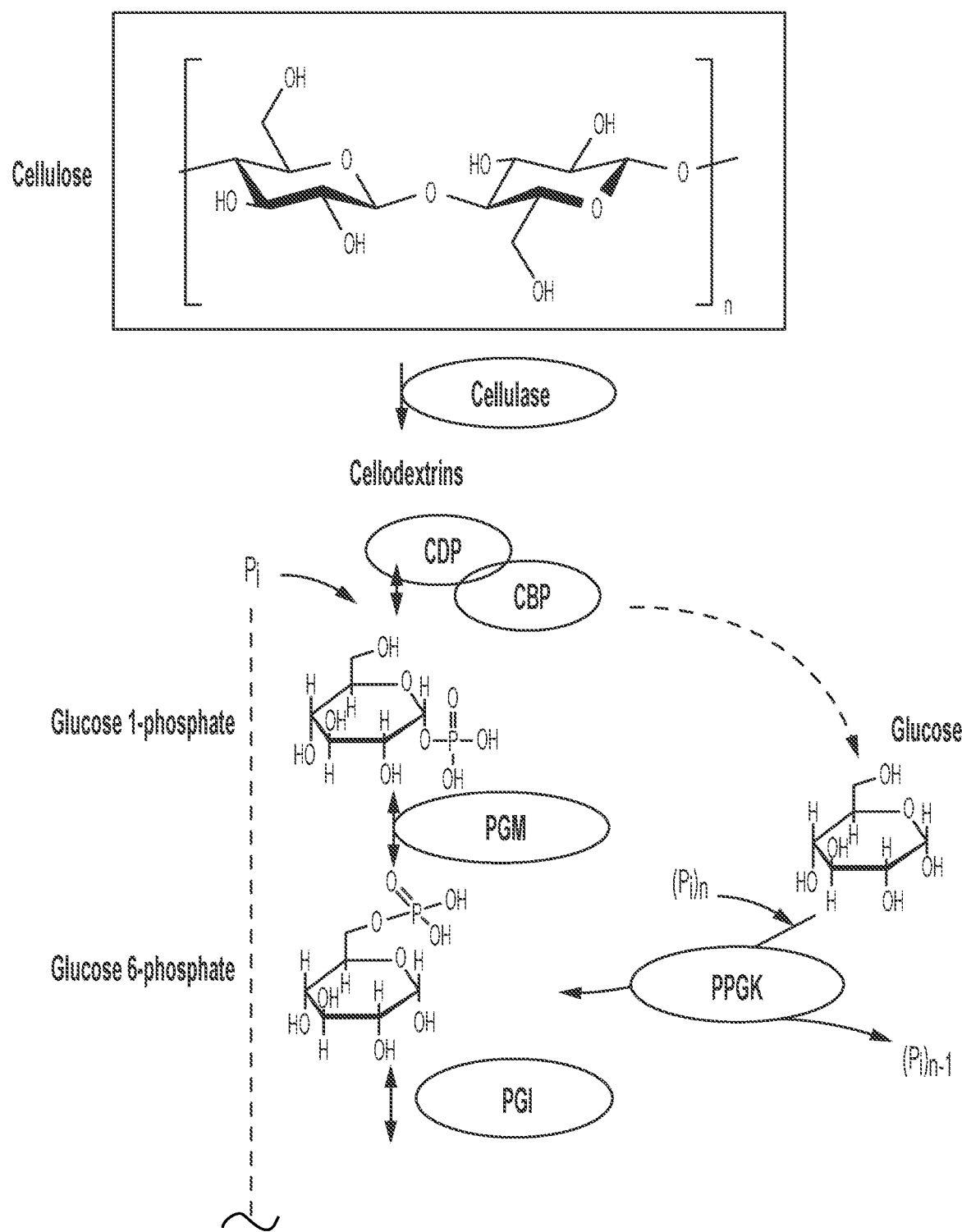
FIG. 3 shows an enzymatic pathway converting cellulose or its derived products to tagatose. CDP, cellodextrin phosphorylase; CBP, cellobiose phosphorylase; PPGK, polyphosphate glucokinase ; PGM, phosphoglucomutase; PGI, phosphoglucoisomerase; F6PE, fructose 6-phosphate epimerase; T6PP, tagatose 6-phosphate phosphatase.
Figure 3:
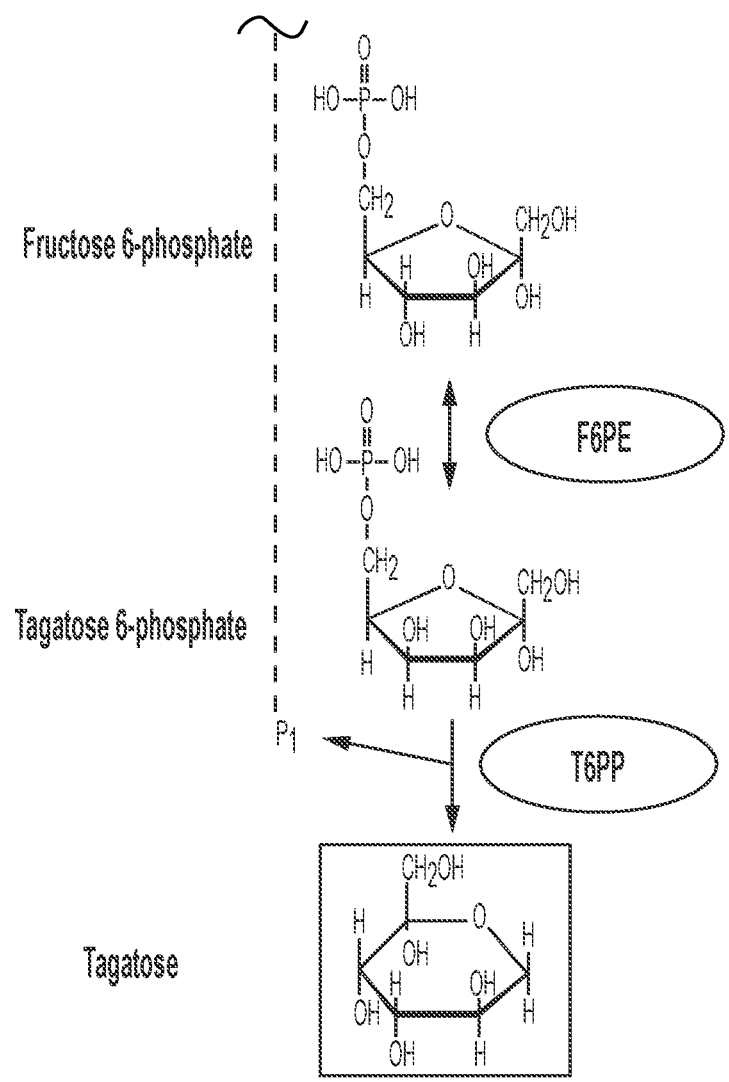

In some embodiments, polyphosphate and polyphosphate glucokinase (PPGK) can be added to the process, thus increasing yields of tagatose by phosphorylating the degradation product glucose to G6P, as shown in FIG. 3.

Figure 5:
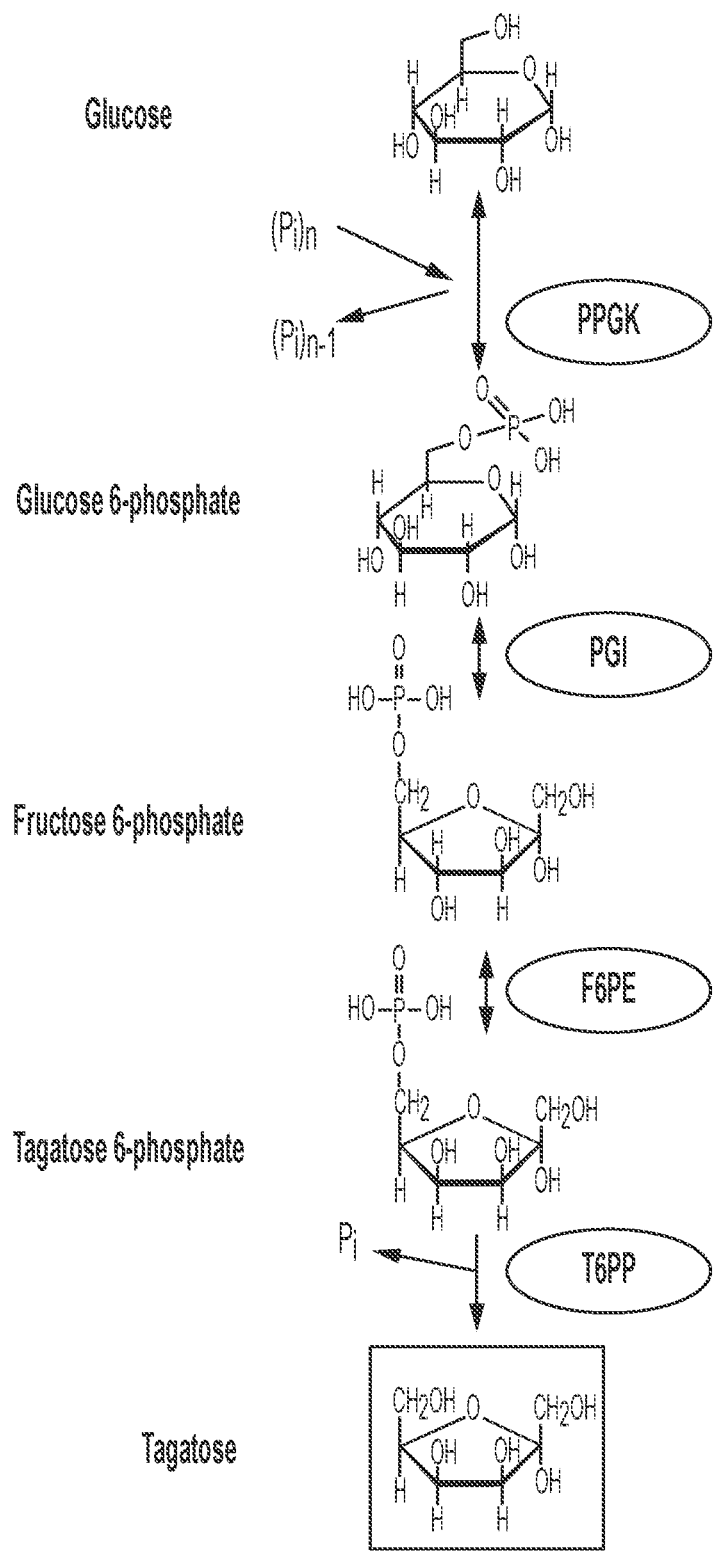
FIG. 5 is a schematic diagram illustrating an enzymatic pathway converting glucose to tagatose. PPGK, polyphosphate glucokinase; PGI, phosphoglucoisomerase; F6PE, fructose 6-phosphate epimerase; T6PP, tagatose 6-phosphate phosphatase.

In other embodiments, tagatose can be generated from glucose. An example of such process is shown in FIG.5. The process involves the steps of generating G6P from glucose and polyphosphate catalyzed by polyphosphate glucokinase (PPGK); converting G6P to F6P catalyzed by PGI; converting F6P to T6P catalyzed by F6PE; and converting T6P to tagatose catalyzed by T6PP.

Any suitable biological buffer known in the art can be used in a process of the invention, such as HEPES, PBS, BIS-TRIS, MOPS, DIPSO, Trizma, etc. The reaction buffer for all embodiments can have a pH ranging from 5.0-8.0. More preferably, the reaction buffer pH can range from about 6.0 to about 7.3. For example, the reaction buffer pH can be 6.0, 6.2, 6.4, 6.6, 6.8, 7.0, 7.2, or 7.3.

The reaction buffer can also contain key metal cations. Examples of the metal ions include $Mg^{2+}$ and $Zn^{2+}$.

The reaction temperature at which the process steps are conducted can range from 37-85° C. More preferably, the steps can be conducted at a temperature ranging from about 40° C. to about 70° C. The temperature can be, for example, about 40° C., about 45° C., about 50° C., about 55° C., or about 60° C. Preferably, the reaction temperature is about 50° C.

The reaction time of the disclosed processes can be adjusted as necessary, and can range from about 8 hours to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

The processes according to the invention can achieve high yields due to the very favorable equilibrium constant for the overall reaction. For example, FIG. 7 shows the Reaction Gibbs Energy between intermediates based on formation Gibbs energy for the conversion of glucose 1-phosphate to tagatose. Reaction Gibbs Energies were generated using http://equilibrator.weizmann.ac.il/. Theoretically, up to 99% yields can be achieved if the starting material is completely converted to an intermediate.

Processes of the invention use low-cost starting materials and reduce production costs by decreasing costs associated with the feedstock and product separation. Starch, cellulose, sucrose and their derivatives are less expensive feedstocks than, for example, lactose. When tagatose is produced from lactose, glucose and galactose and tagatose are separated via chromatography, which leads to higher production costs.

Also, the step of converting T6P to tagatose according to the invention is an irreversible phosphatase reaction, regardless of the feedstock. Therefore, tagatose is produced with a very high yield while effectively minimizing the subsequent product separation costs.

In contrast to cell-based manufacturing methods, the invention involves a cell-free preparation of tagatose, has relatively high reaction rates due to the elimination of the cell membrane, which often slows down the transport of substrate/product into and out of the cell. It also has a final product free of nutrient-rich fermentation media/cellular metabolites.

EXAMPLES

Materials and Methods

Chemicals

All chemicals, including corn starch, soluble starch, maltodextrins, maltose, glucose, filter paper were reagent grade or higher and purchased from Sigma-Aldrich (St. Louis, Mo., USA) or Fisher Scientific (Pittsburgh, Pa., USA), unless otherwise noted. Restriction enzymes, T4 ligase, and Phusion DNA polymerase were purchased from New England Biolabs (Ipswich, Mass., USA). Oligonucleotides were synthesized either by Integrated DNA Technologies (Coralville, Iowa, USA) or Eurofins MWG Operon (Huntsville, Al., USA). Regenerated amorphous cellulose used in enzyme purification was prepared from Avicel PH105 (FMC BioPolymer, Philadelphia, Pa., USA) through its dissolution and regeneration, as described in: Ye et al., *Fusion of a family 9 cellulose-binding module improves catalytic potential of Clostridium thermocellum cellodextrin phosphorylase on insoluble cellulose*. Appl. Microbiol. Biotechnol. 2011; 92:551-560. *Escherichia coli* Sig10 (Sigma-Aldrich, St. Louis, Mo., USA) was used as a host cell for DNA manipulation and *E. coli* BL21 (DE3) (Sigma-Aldrich, St. Louis, Mo., USA) was used as a host cell for recombinant protein expression. ZYM-5052 media including either 100 mg $L^{-1}$ ampicillin or 50 mg $L^{-1}$ kanamycin was used for *E. coli* cell growth and recombinant protein expression. Cellulase from *Trichoderma reesei* (Catalog number: C2730) and pullulanase (Catalog number: P1067) were purchased from Sigma-Aldrich (St. Louis, Mo., USA) and produced by Novozymes (Franklinton, N.C., USA). Maltose phosphorylase (Catalog number: M8284) was purchased from Sigma-Aldrich.

Production and Purification of Recombinant Enzymes

The *E. coli* BL21 (DE3) strain harboring a protein expression plasmid was incubated in a 1-L Erlenmeyer flask with 100 mL of ZYM-5052 media containing either 100 mg $L^{-1}$ ampicillin or 50 mg $L^{-1}$ kanamycin. Cells were grown at 37° C. with rotary shaking at 220 rpm for 16-24 hours. The cells were harvested by centrifugation at 12° C. and washed once with either 20 mM HEPES (pH 7.5) containing 50 mM NaCl and 5 mM $MgCl_2$ (heat precipitation and cellulose-binding module) or 20 mM HEPES (pH 7.5) containing 300 mM NaCl and 5 mM imidazole (Ni purification). The cell pellets were re-suspended in the same buffer and lysed by ultra-sonication (Fisher Scientific Sonic Dismembrator Model 500; 5 s pulse on and 10 s off, total 21 min at 50% amplitude). After centrifugation, the target proteins in the supernatants were purified.

Three approaches were used to purify the various recombinant proteins. His-tagged proteins were purified by the Profinity IMAC Ni-Charged Resin (Bio-Rad, Hercules, Calif., USA). Fusion proteins containing a cellulose-binding module (CBM) and self-cleavage intein were purified through high-affinity adsorption on a large surface-area regenerated amorphous cellulose. Heat precipitation at 70-95° C. for 5-30 min was used to purify hyperthermostable enzymes. The purity of the recombinant proteins was examined by sodium dodecyl sulfate polyacrylamide gel electrophoresis (SDS-PAGE).

Enzymes Used and Their Activity Assays

Alpha-glucan phosphorylase (αGP) from Thermotoga maritima (Uniprot ID G4FEH8) was used. Activity was assayed in 50 mM sodium phosphate buffer (pH 7.2) containing 1 mM MgCl$_2$, 5 mM DTT, and 30 mM maltodextrin at 50° C. The reaction was stopped via filtration of enzyme with a Vivaspin 2 concentrator (10,000 MWCO) (Vivaproducts, Inc., Littleton, Mass., USA). Glucose 1-phosphate (G1P) was measured using a glucose hexokinase/G6PDH assay kit (Sigma Aldrich, Catalog No. GAHK20-1KT) supplemented with 25 U/mL phosphoglucomutase. A unit (U) is described as µmol/min.

Phosphoglucomutase (PGM) from *Thermococcus kodakaraensis* (Uniprot ID Q68BJ6) was used. Activity was measured in 50 mM HEPES buffer (pH 7.2) containing 5 mM MgCl$_2$ and 5 mM G1P at 50° C. The reaction was stopped via filtration of enzyme with a Vivaspin 2 concentrator (10,000 MWCO). The product glucose 6-phosphate (G6P) was determined using a hexokinase/G6PDH assay kit (Sigma Aldrich, Catalog No. GAHK20-1KT).

Two different sources of phosphoglucoisomerase (PGI) were used from *Clostridium thermocellum* (Uniprot ID A3DBX9) and *Thermus thermophilus* (Uniprot ID Q5SLL6). Activity was measured in 50 mM HEPES buffer (pH 7.2) containing 5 mM MgCl$_2$ and 10 mM G6P at 50° C. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P. This 200 µL reaction contained 50 mM HEPES (pH 7.2), 5 mM MgCl$_2$, 10 mM G6P, 1.5 mM ATP, 1.5 mM phosphoenol pyruvate, 200 µM NADH, 0.1 U PGI, 5 U PK, and 5 U LD.

Fructose 6-phosphate epimerase (F6PE) from *Dictyoglomus thermophilum* (Uniprot ID B5YBD7) was used. Activity was measured in 50 mM HEPES buffer (pH 7.2) containing 5 mM MgCl$_2$, and 10 mM F6P at 50° C. The reaction was stopped via filtration of enzyme with a Vivaspin 2 concentrator (10,000 MWCO). The product, tagatose 6-phosphate (T6P), was determined using tagatose 6-phosphate phosphatase and detecting free phosphate release. To detect free phosphate release, 500 µL of a solution containing 0.1 M zinc acetate and 2 mM ammonium molybdate (pH 5) was added to 50 µL of reaction. This was mixed and followed by 125 µL of 5% ascorbic acid (pH 5). This solution was mixed then incubated at 30° C. for 20 min. The absorbance at 850 nm was read to determine free phosphate release.

Thermophilic F6PE from *Anaerolinea thermophila* UNI-1 (Uniprot ID: E8N0N6)

Nucleotide Sequence
(SEQ ID NO.: 1)
ATGTTCGGCTCGCCTGCTCCCCTGCTGGATATGGTCACCGCGCAGAAACA

GGGCATGGCGCGGGGTATCCCATCCATTTGTTCGGCACATCCGGTGGTGC

TGAGTGCCGCCTGCCATCTTGCCCGCCGGAGCGGCGCGCCCCTGCTCATC

GAAACCACCTGCAATCAGGTCAACCACCAAGGTGGGTACAGCGGCATGAC

CCCCGCCGATTTTGTCCGCTTTCTGCGCGAAATTCTGGAACGGGAAGGTA

TTCCCCCGCAACAGGTCATCCTGGGCGGGGATCACCTGGGTCCTTACCCC

TGGCGGAAAGAGCCTGCCGAAACCGCCATAGCACAAGCGCTGGAAATGGT

GCGGGCATACGTGCAGGCAGGCTACACCAAAATTCATCTGGACGCTTCCA

TGCCCTGCGCCGATGACGACCCCGAGCGTCCCCTGCCGCTGGAGCGCATA

GCCCGACGGGCGGCGCAGTTGTGCGCCGCCGCCGAAGCCGCCGCGGGAGC

GGTTCAGCCGGTGTACGTAATTGGCAGTGAGGTGCCCCCGCCCGGCGGCG

CGCAGGGTCAGGAGGCAAGACTTCACGTCACCACTCCGCAGGAAGCCCAA

GCCGCGCTGGATGCCTTTCGGGAAGCCTTTCTGCAGGCAGGCTTGACTCC

CGTTTGGGAGCGGGTCATTGCGCTGGTAGTCCAGCCGGGGGTGGAGTTTG

GCGTGGACAGCATTCACGCCTATCAGCGCGAAGCCGCCCGCCCGCTGAAG

ACCTTCATCGAGGGCGTGCCCGGCATGGTGTATGAAGCCCACTCGACCGA

TTACCAGACCCGTGCCTCCCTGCGTGCGCTGGTGGAAGACCACTTTTCCA

TTCTCAAGGTTGGTCCGGCACTAACCTTTGCCTACCGCGAAGCCGTGTTC

GCCCTGGAACACATCGAACGGGAAATATTGGGCAGGCAGGATATGCCTCT

CTCCCGCCTGAGTGAAGTCCTCGACGAGGTGATGCTGAACGATCCACGCC

ACTGGCAGGGATACTTTGCCGGCGCTCCCGCCGAACAGGCGCTGGCGCGC

CGCTACAGTTTCAGCGACCGCATTCGCTATTACTGGCACCATCCCGCCGC

GCAGGAAGCCGTGCGGAGACTGCTCGCCAACCTGATCGAAACCCCGCCGC

CGCTGAGTTTGCTCAGCCAGTACCTGCCGCGCGAGTATGAGATGGTGCGC

GCGGGGGAAATCTCCAGCCACCCGCAGGACCTGATTCGGGCACATATCCA

GCACACGCTGGAAGATTACGCTGCGGCGTGCGGGTAA

Amino acid sequence
(SEQ ID NO.: 2)
MFGSPAPLLDMVTAQKQGMARGIPSICSAHPVVLSAACHLARRSGAPLLI

ETTCNQVNHQGGYSGMTPADFVRFLREILEREGIPPQQVILGGDHLGPYP

WRKEPAETAIAQALEMVRAYVQAGYTKIHLDASMPCADDDPERPLPLERI

ARRAAQLCAAAEAAAGAVQPVYVIGSEVPPPGGAQGQEARLHVTTPQEAQ

AALDAFREAFLQAGLTPVWERVIALVVQPGVEFGVDSIHAYQREAARPLK

TFIEGVPGMVYEAHSTDYQTRASLRALVEDHFSILKVGPALTFAYREAVF

ALEHIEREILGRQDMPLSRLSEVLDEVMLNDPRHWQYFAGAPAEQALARR

YSFSDRIRYYWHHPAAQEAVRRLLANLIETPPPLSLLSQYLPREYEMVRA

GEISSHPQDLIRAHIQHTLEDYAAACG

Thermophilic F6PE from *Caldicellulosiruptor kronotskyensis* (Uniprot ID: E4SEH3)

Nucleotide sequence
(SEQ ID NO.: 3)
ATGAGTCCTCAAAATCCATTGATTGGTTTATTTAAGAATAGAGAAAAAGA

GTTTAAGGGTATTATTTCAGTTTGTTCTTCAAATGAAATAGTCTTAGAAG

CAGTTTTAAAAAGAATGAAAGATACAAACCTACCAATTATTATTGAAGCC

ACAGCGAACCAGGTAAATCAATTTGGCGGGTATTCTGGGTTGACACCGTC

TCAGTTCAAAGAACGAGTTATAAAAATTGCTCAAAAAGTTGATTTTCCAC

TTGAGAGAATAATTCTTGGTGGGGACCATCTTGGACCATTTGTGTGGCGT

-continued

```
GACCAGGAACCAGAAATTGCTATGGAGTATGCTAAGCAAATGATAAAAGA
ATACATAAAAGCAGGTTTTACCAAAATTCACATCGACACGAGTATGCCTT
TAAAAGGGGAGAACAGCATAGATGATGAAATAATTGCTAAAAGAACTGCT
GTGCTCTGCAGGATTGCGGAGGAGTGTTTTGAGAAGATTTCTATAAACAA
TCCCTATATTACAAGGCCAGTTTATGTGATAGGAGCTGATGTGCCACCTC
CCGGCGGAGAGTCTTCTATTTGTCAAACAATTACTACTAAAGATGAATTA
GAAAGAAGTTTAGAATATTTCAAAGAAGCATTTAAAAAGGAAGGAATTGA
GCATGTATTCGATTATGTAGTTGCTGTTGTTGCAAATTTTGGAGTTGAAT
TTGGGAGCGATGAAATTGTTGATTTTGATATGGAAAAAGTAAAGCCGCTA
AAAGAACTTTTGGCAAAGTACAATATAGTATTTGAAGGCCATTCTACAGA
TTATCAAACAAAAGAAAACTTAAAAAGAATGGTCGAATGTGGTATTGCAA
TTTTAAAGGTTGGTCCTGCTCTAACATTTACATTGCGCGAAGCGTTAGTA
GCACTTAGTCATATTGAAGAAGAAATTTATAGCAATGAAAAGGAGAAACT
GTCAAGATTAGAGAAGTTTTATTGAATACTATGCTAACATGCAAAGATC
ACTGGAGTAAATATTTTGATGAGAATGATAAGTTAATTAAGTCAAAGCTC
CTATATAGCTATCTTGACAGATGGAGATACTATTTTGAAAACGAGAGTGT
GAAAAGTGCTGTTTATTCTCTTATTGGAAATTTAGAGAATGTTAAAATTC
CACCTTGGCTTGTAAGTCAGTATTTTCCTTCTCAGTACCAAAAGATGAGA
AAAAAAGATTTAAAAAACGGTGCTGCCGACCTAATATTGGATAAAATAGG
GGAAGTCATTGACCATTATGTTTATGCGGTAAAAGAATAA
```

Amino acid sequence
(SEQ ID NO.: 4)
MSPQNPLIGLFKNREKEFKGIISVCSSNEIVLEAVLKRMKDTNLPIIIEA
TANQVNQFGGYSGLTPSQFKERVIKIAQKVDFPLERIILGGDHLGPFVWR
DQEPEIAMEYAKQMIKEYIKAGFTKIHIDTSMPLKGENSIDDEIIAKRTA
VLCRIAEECFEKISINNPYITRPVYVIGADVPPPGGESSICQTITTKDEL
ERSLEYFKEAFKKEGIEHVFDYVVAVVANFGVEFGSDEIVDFDMEKVKPL
KELLAKYNIVFEGHSTDYQTKENLKRMVECGIAILKVGPALTFTLREALV
ALSHIEEEIYSNEKEKLSRFREVLLNTMLTCKDHWSKYFDENDKLIKSKL
LYSYLDRWRYYFENESVKSAVYSLIGNLENVKIPPWLVSQYFPSQYQKMR
KKDLKNGAADLILDKIGEVIDHYVYAVKE Thermophilic F6PE from *Caldilinea aerophile* (Uniprot ID: 101507)

Nucleotide sequence
(SEQ ID NO.: 5)
```
ATGTCAACACTTCGCCACATCATTTTGCGACTGATCGAGCTGCGTGAACG
AGAACAGATCCATCTCACGCTGCTGGCCGTCTGTCCCAACTCGGCGGCGG
TGCTGGAGGCAGCGGTGAAGGTCGCCGCGCGCTGCCACACGCCGATGCTC
TTCGCTGCCACGCTCAATCAAGTCGATCGCGACGGCGGCTACACCGGTTG
GACGCCTGCGCAATTCGTCGCCGAGATGCGTCGCTATGCCGTCCGCTATG
GCTGCACCACCCCGCTCTATCCTTGCCTGGATCACGGCGGGCCGTGGCTC
AAAGATCGCCATGCACAGGAAAGCTACCGCTCGACCAGGCGATGCATGA
```

-continued

```
GGTCAAGCTGAGCCTCACCGCCTGTCTGGAGGCCGGCTACGCGCTGCTGC
ACATCGACCCCACGGTCGATCGCACGCTCCCGCCCGGAGAAGCGCCGCTC
GTGCCGATCGTCGTCGAGCGCACGGTCGAGCTGATCGAACATGCCGAACA
GGAGCGACAGCGGCTGAACCTGCCGGCGGTCGCCTATGAAGTCGGCACCG
AAGAAGTACATGGCGGGCTGGTGAATTTCGACAATTTTGTCGCCTTCTTG
GATTTGCTCAAGGCAAGGCTTGAACAACGTGCCCTGATGCACGCCTGGCC
CGCCTTCGTGGTGGCGCAGGTCGGCACTGACCTGCATACAACGTATTTTG
ACCCCAGTGCGGCGCAACGGCTGACTGAGATCGTGCGCCCTACCGGTGCA
CTGTTGAAGGGGCACTACACCGACTGGGTCGAAAATCCCGCCGACTATCC
GAGGGTAGGCATGGGAGGCGCCAACGTTGGTCCAGAGTTTACGGCGGCCG
AGTTCGAGGCGCTGGAAGCGCTGGAACGGCGGGAACAACGGCTGTGCGCC
AACCGGAAATTGCAGCCCGCCTGTTTTTTGGCTGCACTGGAAGAGGCAGT
AGTCGCTTCAGATCGTTGGCGGAAGTGGCTCCAGCCCGATGAGATCGGCA
AGCCCTTTGCAGAATTAACGCCCGCACGCCGGCGCTGGCTCGTGCAGACC
GGGGCACGCTACGTCTGGACTGCGCCGAAAGTTATCGCCGCACGCGAACA
GCTCTATGCGCACCTCTCCCTTGTGCAGGCGGATCCACATGCCTACGTGG
TAGAGTCAGTCGCCCGGTCAATCGAGCGCTATATCGATGCCTTCAACTTA
TACGACGCCGCTACATTGCTTGGATGA
```

Amino acid sequence
(SEQ ID NO.: 6)
MSTLRHIILRLIELREREQIHLTLLAVCPNSAAVLEAAVKVAARCHTPML
FAATLNQVDRDGGYTGWTPAQFVAEMRRYAVRYGCTTPLYPCLDHGGPWL
KDRHAQEKLPLDQAMHEVKLSLTACLEAGYALLHIDPTVDRTLPPGEAPL
VPIVVERTVELIEHAEQERQRLNLPAVAYEVGTEEVHGGLVNFDNFVAFL
DLLKARLEQRALMHAWPAFVVAQVGTDLHTTYFDPSAAQRLTEIVRPTGA
LLKGHYTDWVENPADYPRVGMGGANVGPEFTAAEFEALEALERREQRLCA
NRKLQPACFLAALEEAVVASDRWRKWLQPDEIGKPFAELTPARRRWLVQT
GARYVWTAPKVIAAREQLYAHLSLVQADPHAYVVESVARSIERYIDAFNL
YDAATLLG Thermophilic F6PE from *Caldithrix abyssi* (Uniprot ID: H1XRG1)

Nucleotide sequence
(SEQ ID NO.: 7)
```
ATGAGTCTGCATCCTTTAAATAAATTAATCGAGCGACACAAAAAGGAAC
GCCGGTCGGTATTTATTCCGTCTGTTCGGCCAATCCCTTTGTTTTGAAAG
CGGCCATGCTACAGGCGCAAAAGGATCAGTCTTTGCTACTTATTGAGGCC
ACTTCCAACCAGGTAGATCAATTCGGCGGTTACACCGGCATGCGGCCCGA
AGATTTTAAAACAATGACGCTTGAACTGGCAGCCGAAAACAATTACGATC
CACAGGGATTAATCCTGGGCGGCGACCATCTGGGGCCCAACCGCTGGACA
AAACTGAGCGCCTCCCGGGCCATGGACTACGCCAGAGAGCAGATTGCCGC
TTATGTTAAAGCCGGCTTTTCCAAAATCCACTTAGACGCCACCATGCCCT
TGCAAAACGATGCCACAGATTCCGCCGGCCGCCTTCCAGTCGAAACAATC
```

GCTCAACGTACCGCAGAATTATGCGCCGTGGCCGAACAAACTTACCGGCA
GAGCGACCAACTCTTTCCGCCGCCTGTTTACATTGTCGGCAGCGACGTGC
CCATCCCGGGCGGCGCGCAAGAAGCGCTGAACCAGATCCATATTACGGAG
GTAAAAGAGGTTCAACAGACCATTGATCACGTGCGGCGGGCCTTTGAAAA
AAACGGCCTGGAAGCGGCTTACGAAAGAGTTTGCGCCGTTGTCGTGCAGC
CAGGCGTTGAATTCGCCGATCAAATCGTTTTTGAATACGCTCCCGACAGA
GCGGCGGCCTTAAAAGATTTTATTGAAAGCCATTCGCAGCTGGTTTATGA
AGCGCACTCTACTGATTACCAGACCGCACCTCTTTTGCGCCAGATGGTAA
AAGATCACTTTGCCATTTTAAAGGTCGGGCCTGCGCTCACCTTTGCCCTG
CGCGAAGCCATTTTTGCTCTGGCCTTTATGGAAAAAGAGCTTTTGCCATT
GCACAGAGCGCTCAAACCTTCTGCCATTCTGGAAACGCTGGACCAAACGA
TGGACAAAAACCCTGCTTACTGGCAAAAGCATTACGCGGAACAAAGGAA
GAAGTACGCTTTGCGCAGCGGTTTAGCCTGAGCGACCGCATTCGTTACTA
CTGGCCGTTTCCAAAGGTTCAAAAGGCCCTGCGCCAATTGCTAAAAAACT
TGCAACAAATTTCCATTCCTCTAACTTTGGTAAGCCAGTTCATGCCAGAG
GAATACCAACGTATTCGCCAAGGAACGTTAACCAACGATCCGCAGGCGCT
GATTTTGAACAAAATTCAAAGCGTATTAAAGCAATACGCGGAGGCGACGC
AAATTCAAAACTCTTTGACATTCACGCAAAATCAAAATTCATTAGCAATG
GAGCGACTATGA

Amino acid sequence
(SEQ ID NO.: 8)
MSLHPLNKLIERHKKGTPVGIYSVCSANPFVLKAAMLQAQKDQSLLLIEA
TSNQVDQFGGYTGMRPEDFKTMTLELAAENNYDPQGLILGGDHLGPNRWT
KLSASRAMDYAREQIAAYVKAGFSKIHLDATMPLQNDATDSAGRLPVETI
AQRTAELCAVAEQTYRQSDQLFPPPVYIVGSDVPIPGGAQEALNQIHITE
VKEVQQTIDHVRRAFEKNGLEAAYERVCAVVVQPGVEFADQIVFEYAPDR
AAALKDFIESHSQLVYEAHSTDYQTAPLLRQMVKDHFAILKVGPALTFAL
REAIFALAFMEKELLPLHRALKPSAILETLDQTMDKNPAYWQKHYGGTKE
EVRFAQRFSLSDRIRYYWPFPKVQKALRQLLKNLQQISIPLTLVSQFMPE
EYQRIRQGTLTNDPQALILNKIQSVLKQYAEATQIQNSLTFTQNQNSLAM
ERL Thermophilic F6PE from *Dictyoglomus thermophilum*
(Uniprot ID: B5YBD7)

Nucleotide sequence
(SEQ ID NO.: 9)
ATGTGGCTTAGTAAAGATTATTTGAGAAAAAAGGGAGTTTATTCTATATG
TAGCTCTAATCCATATGTGATTGAGGCAAGTGTTGAATTTGCTAAGGAGA
AGAATGATTATATTTTAATTGAGGCGACACCTCATCAGATAAACCAGTTT
GGTGGATATTCAGGTATGACTCCCGAAGATTTTAAAAACTTTGTAATGGG
AATAATAAAGAAAAGGGAATAGAAGAGGATAGGGTGATTCTTGGAGGGG
ACCATTTAGGCCCTCTCCCTTGGCAAGATGAACCTTCTTCTTCTGCAATG
AAAAAGGCAAAAGACCTTATAAGGGCCTTTGTGGAGAGTGGTTATAAGAA
GATACACCTTGATTGTAGTATGTCTCTTTCTGATGATCCTGTAGTGCTCT
CTCCCGAGAAGATAGCAGAAAGGGAGAGGGAACTTCTTGAGGTTGCAGAA
GAGACTGCTAGAAAGTACAATTTTCAGCCTGTGTATGTGGTGGGAACTGA
TGTACCGGTAGCTGGAGGAGGCGAAGAGGAAGGTATTACCTCAGTGGAGG
ATTTTAGAGTAGCAATCTCCTCTTTAAAAAAATATTTTGAGGATGTTCCA
AGGATATGGGATAGGATAATTGGTTTTGTAATAATGCTTGGTATAGGTTT
TAATTATGAAAAAGTGTTTGAGTATGACAGGATTAAGGTGAGAAAAATTT
TAGAGGAGGTAAAGAAAGAGAATCTTTTTGTTGAAGGTCACTCTACTGAC
TATCAGACAAAACGTGCATTGAGAGATATGGTAGAGGATGGAGTAAGAAT
TCTTAAGGTTGGTCCTGCTTTAACAGCAAGTTTTAGAAGGGGAGTATTTT
TATTAAGTAGCATTGAGGATGAGCTTATATCGGAAGATAAAAGGTCTAAT
ATTAAGAAAGTTGTGCTTGAGACTATGTTAAAAGATGATAAATATTGGAG
AAAGTATTATAAGGATTCAGAAAGATTAGAATTAGATATTTGGTACAACT
TACTTGATAGGATTAGATATTATTGGGAATATAAAGAGATAAAAATAGCT
TTAAATAGGCTTTTTGAAAATTTTTCGGAAGGGGTTGATATTAGATACAT
CTATCAATATTTTTATGATTCGTATTTTAAAGTAAGAGAAGGAAAAATAA
GAAATGATCCAAGGGAGCTAATAAAGAATGAAATAAAGAAGGTCTTGGAG
GACTATACTATGCTGTAAACTTATAA Codon optimized nucleotide sequence
(SEQ ID NO.: 10)
ATGTGGCTGAGCAAGGACTACCTGCGTAAGAAGGGCGTTTACAGCATTTG
CAGCAGCAACCCGTATGTTATTGAAGCGAGCGTGGAGTTCGCGAAGGAGA
AAAACGATTACATCCTGATTGAAGCGACCCCGCACCAGATCAACCAATTT
GGTGGCTATAGCGGCATGACCCCGGAGGACTTCAAGAACTTTGTTATGGG
CATCATTAAGGAAAAAGGTATCGAGGAAGACCGTGTGATTCTGGGTGGCG
ATCACCTGGGTCCGCTGCCGTGGCAGGATGAGCCGAGCAGCAGCGCGATG
AAGAAAGCGAAAGACCTGATCCGTGCGTTCGTTGAAAGCGGTTACAAGAA
AATTCACCTGGATTGCAGCATGAGCCTGAGCGACGATCCGGTGGTTCTGA
GCCCGGAGAAGATCGCGGAACGTGAGCGTGAACTGCTGGAAGTTGCGGAG
GAAACCGCGCGTAAATACAACTTTCAACCGGTGTATGTGGTGGGTACCGA
TGTTCCGGTTGCGGGTGGCGGTGAGGAAGAGGGTATCACCAGCGTGGAGG
ACTTCCGTGTTGCGATTAGCAGCCTGAAGAAATACTTTGAAGACGTTCCG
CGTATTTGGGATCGTATCATTGGTTTCGTGATCATGCTGGGCATTGGTTT
CAACTACGAGAAGGTGTTTGAATATGATCGTATCAAAGTGCGTAAAATTC
TGGAAGAGGTTAAGAAAGAGAACCTGTTTGTGGAAGGCCACAGCACCGAC
TATCAGACCAAGCGTGCGCTGCGTGACATGGTGGAGGATGGCGTTCGTAT
CCTGAAAGTGGGTCCGGCGCTGACCGCGAGCTTCCGTCGTGGTGTGTTTC
TGCTGAGCAGCATCGAGGACGAACTGATTAGCGAGGATAAACGTAGCAAC
ATTAAGAAAGTGGTTCTGGAAACCATGCTGAAGGACGATAAATACTGGCG
TAAGTACTATAAGGACAGCGAGCGTCTGGAACTGGATATCTGGTACAACC
TGCTGGACCGTATTCGTTACTACTGGGAGTACAAGGAAATCAAGATTGCG

```
CTGAACCGTCTGTTCGAGAACTTTAGCGAAGGCGTTGATATCCGTTACAT

CTACCAATACTTCTACGACAGCTACTTCAAAGTGCGTGAGGGTAAAATCC

GTAACGACCCGCGTGAACTGATTAAGAACGAGATTAAGAAAGTGCTGGAA

GACTACCATTATGCGGTGAACCTGTAA
```

Amino acid sequence (SEQ ID NO.: 11)
```
MWLSKDYLRKKGVYSICSSNPYVIEASVEFAKEKNDYILIEATPHQINQF

GGYSGMTPEDFKNFVMGIIKEKGIEEDRVILGGDHLGPLPWQDEPSSSAM

KKAKDLIRAFVESGYKKIHLDCSMSLSDDPVVLSPEKIAERERELLEVAE

ETARKYNFQPVYVVGTDVPVAGGGEEEGITSVEDFRVAISSLKKYFEDVP

RIWDRIIGFVIMLGIGFNYEKVFEYDRIKVRKILEEVKKENLFVEGHSTD

YQTKRALRDMVEDGVRILKVGPALTASFRRGVFLLSSIEDELISEDKRSN

IKKVVLETMLKDDKYWRKYYKDSERLELDIWYNLLDRIRYYWEYKEIKIA

LNRLFENFSEGVDIRYIYQYFYDSYFKVREGKIRNDPRELIKNEIKKVLE

DYHYAVNL
```

Tagatose 6-phosphate phosphatase (T6PP) from *Archaeoglobus fugidis* (Uniprot ID O29805) was used. Activity was measured in 50 mM HEPES buffer (pH 7.2) containing 5 mM MgCl$_2$ and 10 mM T6P at 50° C. The reaction was stopped via filtration of enzyme with a Vivaspin 2 concentrator (10,000 MWCO). Tagatose production was determined by detecting free phosphate release as described for F6PE.

Thermophilic T6PP from *Archaeoglobus fulgidus* (Uniprot ID:O29805)

Nucleotide sequence (SEQ ID NO.: 12)
```
ATGTTCAAACCAAAGGCCATCGCAGTTGACATAGATGGCACCCTCACCGA

CAGAAAGAGGGCTCTGAACTGCAGGGCTGTTGAAGCTCTCCGCAAGGTAA

AAATTCCCGTGATTTTGGCCACTGGTAACATATCTTGTTTTGCGAGGGCT

GCAGCAAAGCTGATTGGAGTCTCAGACGTGGTAATCTGCGAGAATGGGGG

CGTGGTGAGGTTCGAGTACGATGGGGAGGATATTGTTTTAGGAGATAAAG

AGAAATGCGTTGAGGCTGTGAGGGTGCTTGAGAAACACTATGAGGTTGAG

CTGCTGGACTTCGAATACAGGAAGTCGGAAGTGTGCATGAGGAGGAGCTT

TGACATCAACGAGGCGAGAAAGCTCATTGAGGGGATGGGGGTTAAGCTTG

TGGATTCAGGCTTTGCCTACCACATTATGGATGCTGATGTTAGCAAGGGA

AAAGCTTTGAAGTTCGTTGCCGAGAGGCTTGGTATCAGTTCAGCGGAGTT

TGCAGTTATCGGCGACTCAGAGAACGACATAGACATGTTCAGAGTTGCTG

GATTCGGAATTGCTGTTGCCAATGCCGATGAGAGGCTGAAGGAGTATGCT

GATTTAGTTACGCCATCACCAGACGGCGAGGGGGTTGTTGAGGCTTTGCA

GTTTCTGGGATTGTTGCGGTGA
```

Amino acid sequence (SEQ ID NO.: 13)
```
MFKPKAIAVDIDGTLTDRKRALNCRAVEALRKVKIPVILATGNISCFARA

AAKLIGVSDVVICENGGVVRFEYDGEDIVLGDKEKCVEAVRVLEKHYEVE

LLDFEYRKSEVCMRRSFDINEARKLIEGMGVKLVDSGFAYHIMDADVSKG

KALKFVAERLGISSAEFAVIGDSENDIDMFRVAGFGIAVANADERLKEYA

DLVTPSPDGEGVVEALQFLGLLR
```

T6PP from *Archaeoglobus profundus* (Uniprot ID D2RHV2_ARCPA)

Nucleotide sequence (SEQ ID NO.: 14)
```
GTGTTCAAGGCTTTGGTAGTTGATATAGACGGAACTTTGACGGATAAGAA

GAGGGCAATAAACTGCAGAGCGGTCGAAGCACTTAGAAAACTAAAGATTC

CTGTTGTCTTGGCAACCGGAAACATTTCATGCTTTGCAAGGGCTGTAGCT

AAGATTATAGGTGTTTCCGATATTGTAATAGCTGAGAACGGAGGTGTTGT

CAGATTCAGCTACGACGGAGAGGACATAGTTCTGGGGGATAGAAGTAAAT

GCTTAAGAGCTTTGGAGACACTTAGAAAACGCTTCAAAGTAGAGCTTCTC

GACAACGAATATAGGAAGTCTGAGGTCTGCATGAGGAGGAACTTCCCTAT

AGAGGAAGCTAGAAAGATACTGCCAAAAGATGTTAGAATAGTCGATACAG

GCTTCGCATACCACATAATCGATGCAAATGTCAGCAAGGGGAAGGCTTTG

ATGTTCATAGCCGATAAGCTTGGCTTGGACGTTAAGGATTTCATTGCGAT

AGGTGATTCCGAAAACGACATTGAAATGTTGGAAGTTGCAGGTTTTGGCG

TTGCAGTTGCGAATGCGGATGAAAAGCTTAAGGAGGTAGCGGATTTGGTC

ACATCGAAGCCTAATGGAGACGGAGTTGTCGAAGCTCTTGAGTTCTTGGG

ACTCATTTAG
```

Amino acid sequence (SEQ ID NO.: 15)
```
MFKALVVDIDGTLTDKKRAINCRAVEALRKLKIPVVLATGNISCFARAVA

KIIGVSDIVIAENGGVVRFSYDGEDIVLGDRSKCLRALETLRKRFKVELL

DNEYRKSEVCMRRNFPIEEARKILPKDVRIVDTGFAYHIIDANVSKGKAL

MFIADKLGLDVKDFIAIGDSENDIEMLEVAGFGVAVANADEKLKEVADLV

TSKPNGDGVVEALEFLGLI
```

T6PP from *Archaeoglobus veneficus* (Uniprot ID F2KMK2_ARCVS)

Nucleotide sequence (SEQ ID NO.: 16)
```
ATGCTCCGTCCAAAGGGTCTCGCCATTGACATCGACGGAACCATAACATA

CAGGAATCGAAGCCTGAACTGTAAGGCCGTTGAAGCTCTCAGGAAGGTAA

AAATCCCTGTAGTTCTTGCAACTGGCAACATATCCTGTTTCGCAAGAACT

GCTGCAAAGCTTATAGGCGTCTCAGACATTGTTATATGCGAAAATGGAGG

TATTGTTCGATTCAGCTACGATGGCGACGACATAGTGCTTGGGGACATAA

GCAAATGCCTTAAAGCGGCTGAAATTCTCAAAGAGTACTTTGAAATCGAA

TTCCTTGACGCTGAGTACAGGAAGTCGGAGGTCTGTCTTCGCAGAAACTT

TCCTATTGAAGAGGCGAGGAAATTCTTCACGATGCAAAGCTTGATGTTA

AAATCGTCGATTCAGGTTTTGCGTACCACATAATGGATGCGAAGGTCAGC

AAAGGAAGGGCTCTTGAGTACATAGCTGATGAACTTGGTATAAGTCCGAA

GGAGTTCGCTGCAATTGGTGATTCTGAGAACGACATAGACCTGATTAAGG

CTGCCGGCCTCGGTATTGCCGTTGGAGATGCTGACTTAAAGCTCAAAATG
```

-continued

GAGGCCGACGTGGTAGTCTCGAAGAAGAATGGCGATGGAGTTGTTGAAGC

ACTTGAGCTTCTGGGCTTAATTTAA

Amino acid sequence
(SEQ ID NO.: 17)
MLRPKGLAIDIDGTITYRNRSLNCKAVEALRKVKIPVVLATGNISCFART

AAKLIGVSDIVICENGGIVRFSYDGDDIVLGDISKCLKAAEILKEYFEIE

FLDAEYRKSEVCLRRNFPIEEARKILHDAKLDVKIVDSGFAYHIMDAKVS

KGRALEYIADELGISPKEFAAIGDSENDIDLIKAAGLGIAVGDADLKLKM

EADVVVSKKNGDGVVEALELLGLI

The recombinant cellodextrin phosphorylase and cellobiose phosphorylase from *C. thermocellum* are described in Ye et al. Spontaneous high-yield production of hydrogen from cellulosic materials and water catalyzed by enzyme cocktails. ChemSusChem 2009; 2:149-152. Their activities were assayed as described.

The recombinant polyphosphate glucokinase from *Thermobifida fusca* YX is described in Liao et al., One-step purification and immobilization of thermophilic polyphosphate glucokinase from *Thermobifida fusca* YX: glucose-6-phosphate generation without ATP. Appl. Microbiol. Biotechnol. 2012; 93:1109-1117. Its activities were assayed as described.

The recombinant isoamylase from *Sulfolobus tokodaii* is described in Cheng et al., Doubling power output of starch biobattery treated by the most thermostable isoamylase from an archaeon *Sulfolobus tokodaii*. Scientific Reports 2015; 5:13184. Its activities were assayed as described.

The recombinant 4-alpha-glucanoltransferase from *Thermococcus litoralis* is described in Jeon et al. 4-α-Glucanotransferase from the Hyperthermophilic Archaeon *Thermococcus Litoralis*. Eur. J. Biochem. 1997; 248:171-178. Its activity was measured as described.

Sucrose phosphorylase from *Caldithrix abyssi* (Uniprot H1XT50) was used. Its activity was measured in 50 mM HEPES buffer (pH 7.5) containing 10 mM sucrose and 12 mM organic phosphate. Glucose 1-phosphate (G1P) was measured using a glucose hexokinase/G6PDH assay kit supplemented with 25 U/mL phosphoglucomutase as with alpha-glucan phosphorylase.

Enzyme units used in each Example below can be increased or decreased to adjust the reaction time as desired. For example, if one wanted to perform Example 9 in 8 h instead of 24 h, the units of the enzymes would be increased about 3-fold. Conversely, if one wanted perform example 9 in 48 h instead of 24 h the enzyme units could be decreased about 2-fold. These examples illustrate how the amount of enzyme units can be used to increase or decrease reaction time while maintaining constant productivity.

Example 1

To validate the technical feasibility of the enzymatic biosynthesis of fructose 6-phosphate from starch, three enzymes were recombinantly expressed: alpha-glucan phosphorylase from *T maritima* (Uniprot ID G4FEH8), phosphoglucomutase from *Thermococcus kodakaraensis* (Uniprot ID Q68BJ6), and phosphoisomerase from *Clostridium thermocellum* (Uniprot ID A3DBX9). The recombinant proteins were over-expressed in *E. coli* BL21 (DE3) and purified as described above.

A 0.20 mL reaction mixture containing 10 g/L soluble starch, 50 mM phosphate buffered saline pH 7.2, 5 mM $MgCl_2$, 0.5 mM $ZnCl_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 2

Same tests as in Example 1 (other than reaction temperatures) were carried out from 40 to 80° C. It was found that 10 g/L soluble starch produced 0.9 g/L F6P at 40° C. and 3.6 g/L F6P at 80° C. after 40 hour reactions. These results suggest that increasing reaction temperature for this set of enzymes increased F6P yields, but too high temperature may impair some enzyme activity.

Example 3

It was found that, at 80° C., an enzyme ratio of αGP: PGM: PGI of approximately 1:1:1 resulted in fast F6P generation. It was noted that the enzyme ratio did not influence final F6P concentration greatly if the reaction time was long enough. However, the enzyme ratio affects reaction rates and the total cost of enzymes used in the system.

Example 4

A 0.20 mL reaction mixture containing 10 g/L maltodextrin, 50 mM phosphate buffered saline pH 7.2, 5 mM $MgCl_2$, 0.5 mM $ZnCl_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 5

To test for F6P production from Avicel, Sigma cellulase was used to hydrolyze cellulose at 50° C. To remove beta-glucosidase from commercial cellulase, 10 filter paper units/mL of cellulase was mixed to 10 g/L Avicel at an ice-water bath for 10 min. After centrifugation at 4° C., the supernatant containing beta-glucosidase was decanted. Avicel that was bound with cellulase containing endoglucanase and cellobiohydrolase was resuspended in a citrate buffer (pH 4.8) for hydrolysis at 50° C. for three days. The cellulose hydrolysate was mixed with 5 U/mL cellodextrin phosphorylase, 5 U/L cellobiose phosphorylase, 5 U/mL of αGP, 5 U/mL PGM, and 5 U/mL PGI in a 100 mM HEPES buffer (pH 7.2) containing 10 mM phosphate, 5 mM $MgCl_2$ and 0.5 mM $ZnCl_2$. The reaction was conducted at 60° C. for 72 hours and high concentrations of F6P were found (small amounts of glucose and no cellobiose). F6P was detected using the coupled enzyme assay described above. Glucose was detected using a hexokinase/G6PDH assay kit as described above.

Example 6

To increase F6P yields from Avicel, Avicel was pretreated with concentrated phosphoric acid to produce amorphous cellulose (RAC), as described in Zhang et al. *A transition from cellulose swelling to cellulose dissolution by o-phosphoric acid: evidence from enzymatic hydrolysis and supramolecular structure.* Biomacromolecules 2006; 7:644-648. To remove beta-glucosidase from commercial cellulose, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was resuspended in a citrate buffer (pH 4.8) for hydrolysis at 50° C. for 12 hours. The RAC hydrolysate was mixed with 5 U/mL cellodextrin phosphorylase, 5 U/L cellobiose phosphorylase, 5 U/mL of αGP, 5 U/mL PGM, and 5 U/mL PGI in a 100 mM HEPES buffer (pH 7.2) containing 10 mM phosphate, 5 mM $MgCl_2$ and 0.5 mM $ZnCl_2$. The reaction was conducted at 60° C. for 72 hours. High concentrations of F6P and glucose were recovered because no enzymes were added to convert glucose to F6P. F6P was detected using the coupled enzyme assay described above. Glucose was detected using a hexokinase/G6PDH assay kit as described above.

Example 7

To further increase F6P yields from RAC, polyphosphate glucokinase and polyphosphate were added. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was re-suspended in a citrate buffer (pH 4.8) for hydrolysis at 50° C. was incubated in a citrate buffer (pH 4.8) for hydrolysis at 50° C. for 12 hours. The RAC hydrolysate was mixed with 5 U/mL polyphosphate glucokinase, 5 U/mL cellodextrin phosphorylase, 5 U/mL cellobiose phosphorylase, 5 U/mL of αGP, 5 U/mL PGM, and 5 U/mL PGI in a 100 mM HEPES buffer (pH 7.2) containing 50 mM polyphosphate, 10 mM phosphate, 5 mM $MgCl_2$ and 0.5 mM $ZnCl_2$. The reaction was conducted at 50° C. for 72 hours. F6P was found in high concentrations with only small amounts of glucose now present. F6P was detected using the coupled enzyme assay described above. Glucose was detected using a hexokinase/G6PDH assay kit as described above.

Example 8

To validate tagatose production from F6P, 2 g/L F6P was mixed with 1 U/ml fructose 6-phosphate epimerase (F6PE) and 1 U/ml tagatose 6-phosphate phosphatase (T6PP) in 50 mM HEPES buffer (pH 7.2) containing 5 mM $MgCl_2$. The reaction was incubated for 16 hours at 50° C. 100% conversion of F6P to tagatose is seen via HPLC (Agilent 1100 series) using an Agilent Hi-Plex H-column and refractive index detector. The sample was run in 5 mM $H_2SO_4$ at 0.6 mL/min.

Example 9

To validate production of tagatose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, 0.05 U F6PE, and 0.05 U T6PP was incubated at 50° C. for 24 hours. The reaction was stopped via filtration of enzyme with a Vivaspin 2 concentrator (10,000 MWCO). Tagatose was detected and quantified using an Agilent 1100 series HPLC with refractive index detector and an Agilent Hi-Plex H-column. The mobile phase was 5 mM $H_2SO_4$, which ran at 0.6 mL/min. A yield of 9.2 g/L tagatose was obtained. This equates to 92% of the theoretical yield due to limits of maltodextrin degradation without enzymes such as isoamylase or 4-glucan transferase. Standards of various concentrations of tagatose were used to quantify our yield.

Example 10

A reaction mixture containing 200 g/L maltodextrin, 10 mM acetate buffer (pH 5.5), 5 mM $MgCl_2$, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM $MgCl_2$, 0.05 U of αGP, 0.05 U PGM, 0.05 U PGI, 0.05 U F6PE, and 0.05 U T6PP was incubated at 50° C. for 24 hours. Production of tagatose was quantified as in Example 9. The yield of tagatose was increased to 16 g/L with the pretreatment of maltodextrin by isoamylase. This equates to 80% of the theoretical yield.

Example 11

To further increase tagatose yields from maltodextrin, 0.05 U 4-glucan transferase (4GT) was added to the reaction described in example 9.

A 0.2 mL reaction mixture containing 20 g/L isoamylase treated maltodextrin (see example 9), 50 mM phosphate buffered saline pH 7.2, 5 mM MgCl2, 0.05 U of αGP, 0.05 U PGM, 0.05 U PGI, 0.05 U F6PE, 0.05 U T6PP, and 0.05 U 4GT was incubated at 50° C. for 24 hours. Production of tagatose was quantified as in example 9. The yield of tagatose was increased to 17.7 g/L with the addition of 4GT to IA-treated maltodextrin. This equates to 88.5% of the theoretical yield.

Example 12

To determine the concentration range of phosphate buffered saline (PBS), a 0.20 mL reaction mixture containing 50 g/L maltodextrin; 6.25 mM, 12.5 mM, 25 mM, 37.5 mM, or 50 mM phosphate buffered saline pH 7.2; 5 mM MgCl2; 0.1 U of αGP; 0.1 U PGM; 0.1 U PGI; 0.1 U F6PE; and 0.1 U T6PP was incubated at 50° C. for 6 hours. The short duration ensures completion was not reached, and therefore differences in efficiency could be clearly seen. Production of tagatose was quantified as in example 9. Respectively, a yield of 4.5 g/L, 5.1 g/L, 5.6 g/L, 4.8 g/L, or 4.9 g/L tagatose was obtained for the reactions containing either 6.25 mM, 12.5 mM, 25 mM, 37.5 mM, or 50 mM phosphate buffered saline pH 7.2 (Table 1). These results indicate that a concentration of 25 mM PBS pH 7.2 is ideal for these particular reaction conditions. It is important to note that even the use of 6.25 mM PBS at pH 7.2 results in significant turnover due to phosphate recycling. This shows that the disclosed phosphate recycling methods are able to keep phosphate levels low even at industrial levels of volumetric productivity (e.g., 200-300 g/L maltodextrin).

TABLE 1

| Concentration of PBS pH 7.2 (mM) | g/L of Tagatose |
| --- | --- |
| 6.25 | 4.5 |
| 12.5 | 5.1 |
| 25 | 5.6 |
| 37.5 | 4.8 |
| 50 | 4.9 |

Example 13

To determine the pH range of the cascade reaction, a 0.20 mL reaction mixture containing 50 g/L maltodextrin; 50 mM phosphate buffered saline pH 6.0, 6.2, 6.4, 6.6, 6.8, 7.0 7.2, or 7.3; 5 mM MgCl2; 0.02 U of αGP; 0.02 U PGM; 0.02 U PGI; 0.02 U F6PE; and 0.02 U T6PP was incubated at 50° C. for 16 hours. The units were lowered to ensure completion was not reached, and therefore differences in efficiency could be clearly seen. Production of tagatose was quantified as in example 8. Respectively, a yield of 4.0 g/L, 4.1 g/L 4.2 g/L, 4.1 g/L, 4.4 g/L, 4.1 g/L, 3.8 g/L or 4.0 g/L tagatose was obtained for reactions containing 50 mM phosphate buffered saline at pH 6.0, 6.2, 6.4, 6.6, 6.8, 7.0, 7.2, or 7.3 (Table 2). These results indicate that a pH of 6.8 is ideal for these particular reaction conditions, although the system works through a wide pH range.

TABLE 2

| pH of PBS | g/L of Tagatose |
| --- | --- |
| 6.0 | 4.0 |
| 6.2 | 4.1 |
| 6.4 | 4.2 |
| 6.6 | 4.1 |
| 6.8 | 4.4 |
| 7.0 | 4.1 |
| 7.2 | 3.8 |
| 7.3 | 4.0 |

Example 14

To investigate scale-up, a 20 mL reaction mixture containing 50 g/L isoamylase treated maltodextrin (see Example 9), 50 mM phosphate buffered saline pH 7.2, 5 mM MgCl2, 10 U of αGP, 10 U PGM, 10 U PGI, 10 U F6PE, and 10 U T6PP was incubated at 50° C. for 24 hours. Production of tagatose was quantified as in example 8. The yield of tagatose was 37.6 g/L at the 20 mL scale and 50 g/L maltodextrin. This equates to 75% of the theoretical yield. These results indicate that scale-up to larger reaction volumes will not result in significant loses of yield.

Example 15

To further increase tagatose yields from maltodextrin, 0.05 U maltose phosphorylase is added to the reaction described in Example 9.

Example 16

To further increase tagatose yields from maltodextrin, 0.05 U polyphosphate glucokinase and 75 mM polyphosphate is added to the reaction described in Example 9.

Example 17

To produce tagatose from fructose, a reaction mixture containing 10 g/L fructose, 50 mM Tris buffer pH 7.0, 75 mM polyphosphate, 5 mM MgCl2, 0.05 U fructose polyphosphate kinase, 0.05 U F6PE, and 0.05 U T6PP is incubated at 50° C. for 24 hours. Production of tagatose is quantified as in Example 9.

Example 18

To produce tagatose from glucose, a reaction mixture containing 10 g/L glucose, 50 mM Tris buffer pH 7.0, 75 mM polyphosphate, 5 mM MgCl2, 0.05 U glucose polyphosphate kinase, 0.05 U PGI, 0.05 U F6PE, and 0.05 U T6PP is incubated at 50° C. for 24 hours. Production of tagatose is quantified as in Example 9.

Example 19

To produce tagatose from sucrose, a reaction mixture containing 10 g/L sucrose, 50 mM phosphate buffered saline pH 7.0, 5 mM MgCl2, 0.05 U sucrose phosphorylase, 0.05 PGM, 0.05 U PGI, 0.05 U F6PE, and 0.05 U T6PP is incubated at 50° C. for 24 hours. Production of tagatose is quantified as in Example 9.

Example 20

To further increase yields of tagatose from sucrose, 75 mM polyphosphate and 0.05 polyphosphate fructokinase is added to the reaction mixture in example 15. Production of tagatose is quantified as in Example 9.

What is claimed is:

1. An enzymatic process for preparing tagatose from sucrose, the process comprising:
   (i) converting sucrose to glucose 1-phosphate (G1P) catalyzed by a sucrose phosphorylase (SP);
   (ii) converting G1P to glucose 6-phosphate (G6P) catalyzed by a phosphoglucomutase (PGM);
   (iii) converting G6P to fructose 6-phosphate (F6P) catalyzed by a phosphoglucoisomerase (PGI);
   (iv) converting fructose 6-phosphate (F6P) to tagatose 6-phosphate (T6P) catalyzed by fructose 6-phosphate epimerase (F6PE); and
   (v) converting the T6P produced to tagatose catalyzed by a tagatose 6-phospate phosphatase (T6PP).

2. The process of claim 1, further comprising converting fructose, generated by the phosphorolytic cleavage of sucrose by SP, to F6P catalyzed by a polyphosphate fructokinase (PPFK).

3. The process of claim 1, wherein the F6PE is encoded by a polynucleotide comprising a nucleotide sequence having at least 90%, at least 95%, at least 97%, at least 99%, or 100% sequence identity with SEQ ID NOS. 1, 3, 5, 7, 9, or 10.

4. The process of claim 1, wherein the F6PE comprises an amino acid sequence having at least 90%, at least 95%, at least 97%, at least 99%, or 100% sequence identity with SEQ ID NOS. 2, 4, 6, 8, or 11.

5. The process of claim 1, wherein the T6PP is encoded by a polynucleotide comprising a nucleotide sequence having at least 90%, at least 95%, at least 97%, at least 99%, or 100% sequence identity with SEQ ID NOS.: 12, 14, or 16.

6. The process of claim 1, wherein the T6PP comprises an amino acid sequence having at least 90%, at least 95%, at least 97%, at least 99%, or 100% sequence identity with SEQ ID NOS.: 13, 15, or 17.

7. The process of claim 1, wherein at the process steps are conducted under one or more of the following reaction conditions:
   a temperature ranging from about 37° C. to about 85° C.;
   a pH ranging from about 5.0 to about 8.0; and
   for about 8 hours to about 48 hours.

8. The process of claim 1, wherein the process steps are conducted in one bioreactor or in a plurality of bioreactors arranged in series.

9. The process of claim 1, wherein the process steps are conducted under one or more of the following reaction conditions:
   ATP-free;
   NAD(H)-free;
   at a phosphate concentration from about 0 mM to about 150 mM, wherein the phosphate is recycled; and
   at least one step of the process involves an energetically favorable chemical reaction.

* * * * *